United States Patent
Kim et al.

(10) Patent No.: US 11,013,932 B2
(45) Date of Patent: May 25, 2021

(54) SYSTEM AND METHOD FOR PROVIDING SMART COMMUNICATION DEVICE-BASED LOW LEVEL LIGHT THERAPY SERVICE

(71) Applicants: Color Seven Co., Ltd., Seoul (KR); Nam Gyun Kim, Seoul (KR); Kyoung Jun Park, Seoul (KR); Hea Ja An, Seoul (KR); Han Yeong Oh, Incheon (KR)

(72) Inventors: Nam Gyun Kim, Seoul (KR); Kyoung Jun Park, Seoul (KR); Hea Ja An, Seoul (KR); Han Yeong Oh, Incheon (KR)

(73) Assignees: COLOR SEVEN CO., LTD., Seoul (KR); Nam Gyun Kim, Seoul (KR); Kyoung Jun Park, Seoul (KR); Hea Ja An, Seoul (KR); Han Yeong Oh, Incheon (KR)

( * ) Notice: Subject to any disclaimer, the term of this patent is extended or adjusted under 35 U.S.C. 154(b) by 379 days.

(21) Appl. No.: 15/736,864

(22) PCT Filed: May 10, 2017

(86) PCT No.: PCT/KR2017/004783
§ 371 (c)(1),
(2) Date: Dec. 15, 2017

(87) PCT Pub. No.: WO2017/196052
PCT Pub. Date: Nov. 16, 2017

(65) Prior Publication Data
US 2018/0154167 A1    Jun. 7, 2018

(30) Foreign Application Priority Data
May 11, 2016 (KR) .......... 10-2016-0057680
May 4, 2017 (KR) .......... 10-2017-0056954

(51) Int. Cl.
*A61F 9/008* (2006.01)
*A61N 5/06* (2006.01)
(Continued)

(52) U.S. Cl.
CPC .............. *A61N 5/06* (2013.01); *G06F 9/44* (2013.01); *G06Q 20/127* (2013.01);
(Continued)

(58) Field of Classification Search
CPC .......... A61N 5/06; G16H 10/20; G16H 40/63; G16H 20/70; G06F 9/44; G06Q 20/127;
(Continued)

(56) References Cited

U.S. PATENT DOCUMENTS

2006/0154642 A1* 7/2006 Scannell, Jr. ............ F21V 33/00
455/404.1
2008/0033754 A1* 2/2008 Smith ................... G06F 19/324
705/2
(Continued)

FOREIGN PATENT DOCUMENTS

JP    2014-500538 A    1/2014
JP    2015-529359 A    10/2015
(Continued)

*Primary Examiner* — Michael W Kahelin
*Assistant Examiner* — George E Banis
(74) *Attorney, Agent, or Firm* — Rabin & Berdo, P.C.

(57) ABSTRACT

The present disclosure relates to a system and method for providing a smart communication device-based light therapy service in which a light therapy device is operated in conjunction with a smart communication device and an information providing server to perform a light therapy, and when a user purchases a lightceutical clinical code corresponding to a certain disease using the smart communication device, the information providing server generates the lightceutical clinical code of the disease containing a wavelength (Continued)

of light, an intensity of light, an irradiation time of light, and an irradiation pattern of light and sends the generated lightceutical clinical code to the smart communication device, and the smart communication device sends the received lightceutical clinical code to the light therapy device or generates a light therapy device control signal in accordance with the lightceutical clinical code and transmits the generated light therapy device control signal to the light therapy device to operate the light therapy device, thereby allowing customized therapy of various diseases or symptoms to be performed.

The system for providing a smart communication device-based light therapy service includes a smart communication device through which a screen for purchasing a lightceutical clinical code including a wavelength of light, an intensity of light, an irradiation time of light, and an irradiation pattern of light is output and configured to receive a lightceutical clinical code from an information providing server and send the received lightceutical clinical code to a light therapy device or generate a light therapy device control signal in accordance with the lightceutical clinical code and send the generated light therapy device control signal to the light therapy device when a payment for a purchase of the lightceutical clinical code is completed in conjunction with a financial payment server, the information providing server configured to read the lightceutical clinical code from an information providing server DB and send the read lightceutical clinical code to the smart communication device when the payment for the lightceutical clinical code is completed by the smart communication device operating in conjunction with the financial payment server, and the light therapy device configured to operate in accordance with the lightceutical clinical code or the light therapy device control signal received from the smart communication device.

17 Claims, 19 Drawing Sheets

(51) Int. Cl.
| | |
|---|---|
| *G06Q 20/32* | (2012.01) |
| *G16H 10/20* | (2018.01) |
| *G16H 40/63* | (2018.01) |
| *G16H 20/70* | (2018.01) |
| *G06Q 20/14* | (2012.01) |
| *G06Q 30/06* | (2012.01) |
| *G06Q 50/22* | (2018.01) |
| *H04L 9/32* | (2006.01) |
| *G07F 17/00* | (2006.01) |
| *G07F 17/18* | (2006.01) |
| *G06F 9/44* | (2018.01) |
| *G06Q 20/12* | (2012.01) |
| *G06Q 30/02* | (2012.01) |

(52) U.S. Cl.
CPC ........ *G06Q 20/145* (2013.01); *G06Q 20/325* (2013.01); *G06Q 30/02* (2013.01); *G06Q 30/06* (2013.01); *G06Q 50/22* (2013.01); *G07F 17/0014* (2013.01); *G07F 17/18* (2013.01); *G16H 10/20* (2018.01); *G16H 20/70* (2018.01); *G16H 40/63* (2018.01); *H04L 9/32* (2013.01); *A61N 2005/0626* (2013.01); *A61N 2005/0645* (2013.01); *A61N 2005/0647* (2013.01); *A61N 2005/0651* (2013.01); *A61N 2005/0653* (2013.01)

(58) Field of Classification Search
CPC .... G06Q 20/145; G06Q 20/325; G06Q 30/02; G06Q 30/06; G06Q 50/22; G07F 17/0014; G07F 17/18
See application file for complete search history.

(56) References Cited

U.S. PATENT DOCUMENTS

| | | | |
|---|---|---|---|
| 2009/0082690 A1* | 3/2009 | Phillips | A61B 5/04001 600/544 |
| 2010/0324936 A1* | 12/2010 | Vishnubhatla | G06F 19/328 705/3 |
| 2012/0157889 A1 | 6/2012 | Tanis et al. | |
| 2014/0052465 A1 | 2/2014 | Madan et al. | |
| 2014/0088668 A1* | 3/2014 | Kim | A61N 5/06 607/90 |
| 2015/0012060 A1* | 1/2015 | Liu | A61N 1/37235 607/59 |
| 2015/0227909 A1* | 8/2015 | Laing | G06Q 50/22 705/2 |

FOREIGN PATENT DOCUMENTS

| | | |
|---|---|---|
| KR | 10-1157457 B1 | 6/2012 |
| KR | 10-2013-0005598 A | 1/2013 |
| KR | 10-2013-0065748 A | 6/2013 |
| KR | 10-1385707 B1 | 4/2014 |
| KR | 10-2014-0089720 A | 7/2014 |
| KR | 10-1479576 B1 | 1/2015 |
| KR | 10-2016-0055082 A | 5/2016 |
| KR | 10-2016-0099352 A | 8/2016 |

* cited by examiner

| No | DEVICE NUMBER | DATE OF REGISTRATION | TREATED DISEASE | GENDER | AGE | SKIN COLOR | NUMBER OF TIMES OF THERAPY | REMAINING NUMBER OF TIMES | NOTE |
|---|---|---|---|---|---|---|---|---|---|
| 3 | 15685 | 2015-12-24 | MENSTRUAL PAIN | FEMALE | TEENS TO TWENTIES | Brown | 20 TIMES | 15 TIMES | |
| 2 | 45358 | 2016-01-01 | MENSTRUAL PAIN | FEMALE | TEENS TO TWENTIES | Brown | 20 TIMES | 15 TIMES | |
| 1 | 12345 | 2015-12-12 | MENSTRUAL PAIN | FEMALE | TEENS TO TWENTIES | Brown | 20 TIMES | 10 TIMES | |

SYSTEM AND METHOD FOR PROVIDING SMART COMMUNICATION DEVICE-BASED LOW LEVEL LIGHT THERAPY SERVICE

BACKGROUND

1. Field of the Invention

The present disclosure relates to a system and method for providing a smart communication device-based light therapy service in which a light therapy device is operated in conjunction with a smart communication device and an information providing server to perform a light therapy, and when a user purchases a lightceutical clinical code corresponding to a certain disease using the smart communication device, the information providing server generates the lightceutical clinical code of the disease containing a wavelength of light, an intensity of light, an irradiation time of light, and an irradiation pattern of light and sends the generated lightceutical clinical code to the smart communication device, and the smart communication device sends the received lightceutical clinical code to the light therapy device or generates a light therapy device control signal in accordance with the lightceutical clinical code and transmits the generated light therapy device control signal to the light therapy device to operate the light therapy device, thereby allowing customized therapy of various diseases or symptoms to be conveniently and safely performed anytime and anywhere.

2. Discussion of Related Art

In areas of healthcare where smart phones are being utilized, smartphone manufacturers that produce iPhones and Android phones are launching, in intense international competition, healthcare products that assess step counts, pulse, diabetes, blood pressure, body fat, exercise amount, and the like using smartphones or smart watches in order to diagnose and manage health. However, since the technologies of the products being launched by different manufacturers are very similar, the competition is intense, and it is thus predicted that a manufacturer having a competitive advantage in terms of price will succeed in competition, except for when it comes to exceptional products. Also, other than healthcare products for diagnosing diseases and managing health using smartphones, the large smartphone manufacturers are not offering any products that allow therapy of diseases to be safely and conveniently performed using smartphones anytime and anywhere.

Particularly, mobile healthcare applications in app stores are being more frequently used. Examples of mobile healthcare applications may include a behavior-tracking program, a body information monitoring program, a diet and weight-loss management program, an exercise method providing program, a medical/health information and campaign providing program, a medical information access and reservation management program, a management program for medical personnel, and an integrated health service website. However, most of the healthcare-related applications currently registered in the app store focus on the fitness field utilizing a behavior-tracking function, and healthcare applications specialized for treating specific diseases are rare.

Low level light therapy is already widely known as a method of treating or preventing various diseases by stimulating specific spots of the human body using low level light energy in various wavelength ranges and is widely used for recovering from fatigue, skin care, and the like or in fields such as the alternative medicine field and the pain management field. Nowadays, in the traditional Korean medicine field or the alternative medicine field, low level light therapy is performed for therapy of a specific body part or an internal organ connected to a certain acupuncture spot on a body surface via the peripheral nervous system through stimulation of the acupuncture spot, through which blood in the meridian system gather and pass, using light energy of a light therapy device, therapy of pain, inflammation, or the like (for example, treatment of menstrual pain, burn treatment, or the like), prevention and therapy of stroke and dementia, or health management. Particularly, low level light therapy has advantages in that a therapy device is configured to be simple and safe, the therapy is highly effective, and the therapy device is convenient to use such that anyone, regardless of age or gender, can use the therapy device for treating diseases anytime and anywhere.

Therefore, it is considered that there is an urgent need for a system and method for providing a smart communication device-based low level light therapy service with which anyone, regardless of age or gender, can safely and conveniently mitigate or treat his or her symptoms or diseases anytime and anywhere without seeing a doctor by using the low level light therapy having the above-mentioned advantages and using smart communication devices that the user always carry.

The present applicant has already filed multiple patent applications related to light therapy devices operated in conjunction with smartphones.

Korean Patent Registration No. 10-1157457 discloses a device for relaxing smooth muscles of the human body that includes a wired or wireless electrode probe and can be controlled using a wireless controller. Here, the device for relaxing smooth muscles of the human body is a light therapy device including a controller main body and an electrode probe connected via a wire or wirelessly to the controller main body and configured to emit light, wherein the electrode probe includes a light-emitting diode (LED). Particularly, the device is configured to continuously output light having a specific wavelength of rays of light having wavelengths in the range of 400 nm to 800 nm and is ultimately specialized for treating a single specific spot. Consequently, the device does not allow a user to perform customized therapy each time in accordance with a spot to be treated, pain, or the like.

Korean Patent Registration No. 10-1385707 relates to a color light therapy system that performs color light therapy using visible light by operating a color light therapy device and a portable smart communication device in conjunction with each other. The system is also configured to output light having a specific wavelength and is ultimately specialized for treating a single specific spot. Consequently, the system does not allow a user to perform customized therapy each time in accordance with a spot to be treated, pain, or the like. The color light therapy device is configured to operate by receiving power by being connected to a universal serial bus (USB) terminal or a charger terminal of the portable smart communication device. However, light sufficient for therapy cannot be continuously generated just by simply connecting the color light therapy device as above. Therefore, an operation of the color light therapy device may be somewhat unstable.

Korean Patent Registration No. 10-1479576 discloses a color light therapy operating device built in a portable smart communication device, which is almost identical to the color light therapy system disclosed in Korean Patent Registration No. 10-1385707. That is, even the color light therapy operating device disclosed in Korean Patent Registration No. 10-1479576 does not allow a user to perform customized therapy each time in accordance with a spot to be treated, pain, or the like. Also, a power plug of the color light therapy operating device is connected to an earphone jack of the smart communication device such that the color light therapy operating device operates by receiving power from the smart communication device. However, light sufficient for therapy cannot be continuously generated in this way, and an operation of the color light therapy operating device may be somewhat unstable.

Korean Unexamined Patent Application Publication No. 10-2016-0055082 relates to a smartphone interface device for light therapy that performs communication with a smartphone using a USB on-the-go (OTG) module and a micro controller unit (MCU) installed in the smartphone interface device, thereby more stably controlling and operating a light therapy device. Even in this disclosure, a user is unable to perform customized therapy each time in accordance with a spot to be treated, pain, or the like.

Korean Unexamined Patent Application Publication No. 10-2016-0099352 relates to a method of controlling a portable personal communication terminal connected to a low level light irradiator. This disclosure employs the smartphone interface device for light therapy and the light irradiator (light therapy device) of Korean Unexamined Patent Application Publication No. 10-2016-0055082. Even in this disclosure, a user is unable to perform customized therapy each time in accordance with a spot to be treated, pain, or the like.

Therefore, the present disclosure proposes a system and method for providing a smart communication device-based low level light therapy service in which an information providing server receives a certain disease or symptom to be treated from a smart communication device, generates a lightceutical clinical code and information related to a low level light therapy method (for example, operation information of a low level light therapy device, low level light therapy guide information, and the like), and sends the generated lightceutical clinical code and information related to a low level light therapy method to the smart communication device, and the smart communication device operates the low level light therapy device in accordance with the received lightceutical clinical code and information related to a low level light therapy method. Consequently, a user can perform therapy anytime and anywhere with a light therapy device he or she already owns after just purchasing, using a smart device, a lightceutical clinical code corresponding to a disease or symptom at the time.

FIG. 1 is a view for describing a configuration of a low level light therapy device (100). FIG. 1 is described in Korean Unexamined Patent Application Publication No. 10-2016-0055082.

The low level light therapy device (100) connected to a smart communication device (200) includes a USB OTG module (30), a voltage regulator (40), a MCU (50), a light irradiation operator (60), a light irradiating electrode connector (70), an LED operation indicator light (80), and a light irradiating electrode (71). Here, the USB OTG module (30), the voltage regulator (40), the MCU (50), the light irradiation operator (60), the light irradiating electrode connector (70), and the LED operation indicator light (80) constitute a light therapy device controller (13). The light therapy device controller (13) is a device operated in conjunction with a smartphone to operate the light irradiating electrode (71) and is described as a smartphone interface device in Korean Unexamined Patent Application Publication No. 10-2016-0055082.

The USB OTG module (30) enables communication between the smart communication device (200) and the MCU (50) installed in the low level light therapy device (100) by setting the smart communication device (200) as a host. The USB OTG module (30) connected to the MCU (50) is connected to a smartphone connector, and the smart communication device (200) is set as a host to enable communication between the smart communication device (200) and the MCU (50) installed in the light therapy device (100).

The voltage regulator (40) converts a voltage output from the smart communication device (200) to correspond to an operating voltage of the MCU (50).

The MCU (50) controls an overall operation of the light therapy device (100) and controls a light irradiation intensity, a light irradiation time, a light irradiation pattern, a start and an end of light irradiation, and the like by interpreting a control command from the smart communication device (200) received via the USB OTG module (30). That is, the MCU (50) interprets the control command of the smart communication device (200), generates a light source control signal, and sends the generated light source control signal to the light irradiation operator (60).

The light irradiation operator (60) operates a light source in accordance with the light source control signal received from the MCU (50). The light irradiation operator (60) includes a voltage or current amplifying circuit required to operate the light source.

The LED operation indicator light (80) is a light indicating a state of a light irradiating operation, that is, an LED light indicating that the light irradiating electrode is being operated.

The light irradiating electrode connector (70) is a connector for connecting the light irradiating electrode. The smartphone interface device (100) for light therapy is connected to the light irradiating electrode by the light irradiating electrode connector (70). Here, light irradiating electrodes having various forms may be applied as the light irradiating electrode.

An application for controlling a light irradiation intensity, a light irradiation time, a light irradiation pattern, a start and an end of light irradiation, and the like of the light irradiating electrode is installed in the smart communication device (200).

FIG. 2 illustrates the low level light therapy device (100) connected to the light irradiating electrode of Korean Unexamined Patent Application Publication No. 10-2016-0055082.

The light therapy device (100) includes a smartphone connector (11), a connecting cable (12), the light therapy device controller (13), the LED operation indicator light (80), the light irradiating electrode connector (70), or the like.

The light therapy device controller (13) has the USB OTG module (30), the voltage regulator (40), the MCU (50), and the light irradiation operator (60) embedded therein and has the light irradiating electrode connector (70) disposed at one side and the connecting cable (12) connected to the smartphone connector (11) connected at the other side. The LED operation indicator light (80) is located at an upper surface of the light therapy device controller (13). The smartphone connector (11) and the light irradiating electrode connector (70) may be manufactured in various ways for exclusive use with an audio terminal, a micro USB, or the smartphone interface device for light therapy. Although the smart communication device (200) and the light therapy device (100) are connected via a wire in FIG. 4, the smart communication device (200) and the light therapy device (100) may also be wirelessly connected in some cases.

SUMMARY OF THE INVENTION

An objective of the present disclosure is to provide a system and method for providing a smart communication device-based light therapy service in which a light therapy device is operated in conjunction with a smart communication device and an information providing server to perform a light therapy, and when a user purchases a lightceutical clinical code corresponding to a certain disease using the smart communication device, the information providing server generates the lightceutical clinical code of the disease containing a wavelength of light, an intensity of light, an irradiation time of light, and an irradiation pattern of light and sends the generated lightceutical clinical code to the smart communication device, and the smart communication device sends the received lightceutical clinical code to the light therapy device or generates a light therapy device control signal in accordance with the lightceutical clinical code and transmits the generated light therapy device control signal to the light therapy device to operate the light therapy device, thereby allowing customized therapy of various diseases or symptoms to be conveniently and safely performed anytime and anywhere.

Another objective of the present disclosure is to provide a system and method for providing a smart communication device-based light therapy service in which a function of registering a light therapy device and inputting user information via a user interface (UI) screen, a function of presenting several names of diseases or symptoms and allowing a user to select a disease name or symptom to be treated via a UI screen, a function of providing information on a low level light therapy method related to the selected disease name or symptom to the user with letters, images, photographs, or moving pictures, a function of allowing the user to purchase a lightceutical clinical code of the disease or symptom that he or she wishes to treat using the smart communication device, a function of allowing the user to change the lightceutical clinical code as needed, and a function of performing low level light therapy are performed by the smart communication device.

Still another objective of the present disclosure is to provide a system and method for providing a smart communication device-based light therapy service in which a function of allowing a user to input and store a state of his or her disease or symptom before light therapy via a UI screen, a function of allowing the user to input and store a state of his or her disease or symptom after the light therapy, a function of allowing the user to check the states of his or her disease or symptom before and after the light therapy in graphs or numerical values on a weekly basis, a monthly basis, and a yearly basis, and a function of allowing data input by the user to be sent to an information providing server via wired and wireless information networks and stored in a customer information database (DB) of the information providing server are performed by the smart communication device.

To achieve the above objectives, a system for providing a smart communication device-based light therapy service according to the present disclosure includes a smart communication device through which a screen for purchasing a lightceutical clinical code including a wavelength of light, an intensity of light, an irradiation time of light, and an irradiation pattern of light is output and configured to receive a lightceutical clinical code from an information providing server and send the received lightceutical clinical code to a light therapy device or generate a light therapy device control signal in accordance with the lightceutical clinical code and send the generated light therapy device control signal to the light therapy device when a payment for a purchase of the lightceutical clinical code is completed in conjunction with a financial payment server; the information providing server configured to read the lightceutical clinical code from an information providing server DB and send the read lightceutical clinical code to the smart communication device when the payment for the lightceutical clinical code is completed by the smart communication device operating in conjunction with the financial payment server; and the light therapy device including a light source and configured to operate in accordance with the lightceutical clinical code or the light therapy device control signal received from the smart communication device to irradiate light by a light irradiating electrode.

A number of times that the lightceutical clinical code is usable may be limited. The number of times that the lightceutical clinical code is usable may be stored in the information providing server DB and reduced in accordance with a number of times that the light therapy device is operated.

The lightceutical clinical code may be different in accordance with a disease or symptom.

The smart communication device may be configured to display a disease selection screen through which a name of a disease to be treated is to be selected before the light therapy device is operated, display a notification that a lightceutical clinical code of a selected disease name is not purchased and a pop-up window that asks whether to purchase the lightceutical clinical code of the selected disease name when the lightceutical clinical code of the disease name selected via the disease selection screen has not already been purchased, and output a purchase screen when a switch indicating a decision to purchase the lightceutical clinical code is selected in the pop-up window.

The number of times that the lightceutical clinical code is usable may be displayed on the smart communication device.

When the number of times that the lightceutical clinical code is usable is exhausted, the smart communication device may be configured to display a notification that the number of times that the lightceutical clinical code is usable has been exhausted and a pop-up window that asks whether to purchase the number of times that the lightceutical clinical code is usable and output a purchase screen when a switch indicating a decision to purchase the number of times that the lightceutical clinical code is usable is selected in the pop-up window to allow a payment for an additional purchase of the number of times that the lightceutical clinical code is usable.

Before an operation of the light therapy device is started, the smart communication device may be configured to display a self-diagnosis screen including questionnaire items related to a drug dose of a certain disease and send a response to the self-diagnosis questionnaire input by the user via the self-diagnosis screen to the information providing server, and the information providing server may be configured to store the response to the self-diagnosis questionnaire in the information providing server DB.

When the operation of the light therapy device is ended, the smart communication device may be configured to display a therapy result input screen including questionnaire items related to a degree of pain and send a response to a therapy result questionnaire input by the user via the therapy result input screen to the information providing server, and the information providing server may be configured to store the response to the therapy result questionnaire in the information providing server DB.

The light source of the light therapy device may be any one of a three-color LED, an organic LED (OLED), a quantum dot LED (QLED), and an active matrix OLED (AMOLED).

The smart communication device may be configured to operate the light therapy device through a therapy screen and, upon receiving a lightceutical clinical code, configured to send the changed lightceutical clinical code to the light therapy device or generate a light therapy device control signal in accordance with the changed lightceutical clinical code and send the generated light therapy device control signal to the light therapy device.

A device number of the light therapy device may be registered in the information providing server via the smart communication device.

Upon registering the light therapy device, registration information including the device number of the light therapy device, a password, a gender of the user, an age of the user, and a skin color of the user input via the smart communication device may be sent to the information providing server, and the information providing server may be configured to store the registration information therein.

The smart communication device may display information related to a therapy method using the light therapy device including light irradiating electrode attachment positions in accordance with diseases using letters, images, photographs, or moving pictures.

The smart communication device may be configured to statistically process the response to the therapy result questionnaire or the response to the self-diagnosis questionnaire stored in the information providing server DB and display the responses in weeks, months, and years.

The smart communication device may be any one of a smartphone or smart watch (wrist-worn smartphone) that uses one of Android operating system (OS), Android Wear OS, Android Open Source Project OS, Apple iOS, Tizen OS, MS window OS, BlackBerry OS, FireFox OS, and MiUi Color OS as an OS.

The light therapy device may include the light irradiating electrode and a light therapy device controller and may be mounted in any one of a headgear, a patch, a necklace, a bracelet, a watch, a belt, a wrist band, a glove, a waist support, a shirt, and underpants.

The lightceutical clinical code may be in the form of a number or a combination of numbers and letters by encoding values of the wavelength of light, the intensity of light, the irradiation time of light, and the irradiation pattern of light.

The smart communication device may have a light therapy application received from the information providing server installed therein, and the light therapy application may be on the basis of any one of the Android OS, the Android Wear OS, the Android Open Source Project OS, the Apple iOS, the Tizen OS, the MS window OS, the BlackBerry OS, the FireFox OS, and MiUi Color OS.

Any one of a get method and a post method may be used as a method of transmitting data between the smart communication device and the information providing server to encode the data with any one of an application programming interface (API) method and a Plug-In method and send the data.

A UI language of the light therapy application may be one of languages registered in the United Nations (UN).

Names of diseases presented on a screen of the light therapy application may be those present in the International Classification of Diseases code.

The information related to a therapy method using the light therapy device may further include a light irradiation time per each time, a number of times that light irradiation is performed per day, an average therapy period for each disease, and precautions.

The questionnaire items related to the self-diagnosis screen and the therapy result input screen may comply with questionnaire items of internationally standardized questionnaires.

The smart communication device and the light therapy device may be connected via a wire or wirelessly. When the smart communication device and the light therapy device are wirelessly connected, the smart communication device and the light therapy device are connected using any one of Zigbee, Bluetooth, near-field communication (NFC), wireless fidelity (Wi-Fi), and radio frequency (RF). When the smart communication device and the light therapy device are connected via a wire, the smart communication device and the light therapy device are connected using a USB terminal, an iPhone terminal, Recommended Standard-232C (RS232C), Inter-integrated circuit (I2C), or serial peripheral interface (SPI).

Further, the present disclosure provides an operation method of a system for providing a smart communication device-based light therapy service in which, when a payment for purchasing a lightceutical clinical code including a wavelength of light, an intensity of light, an irradiation time of light, and an irradiation pattern of light is completed in conjunction with a financial payment server in a smart communication device, the smart communication device receives the lightceutical clinical code from an information providing server and sends the received lightceutical clinical code to a light therapy device or generates a light therapy device control signal in accordance with the lightceutical clinical code and sends the generated light therapy device control signal to the light therapy device, and the light therapy device is operated in accordance with the received lightceutical clinical code or light therapy device control signal, the operation method including determining whether a lightceutical clinical code is owned in which the smart communication device determines whether a user has purchased and owns a lightceutical clinical code of a symptom or disease selected by the user via a disease selection screen or a symptom selection screen and determines whether a number of times that the lightceutical clinical code is usable has been exhausted; purchasing a lightceutical clinical code in which, when it is determined that the lightceutical clinical code has not been purchased or the number of times that the lightceutical clinical code is usable has been exhausted in the determining of whether the lightceutical clinical code is owned, the smart communication device displays a notification that the lightceutical clinical code has not already been purchased or the number of times that the lightceutical clinical code is usable has been exhausted and a pop-up window that asks whether to purchase the lightceutical clinical code, outputs a purchase screen when a switch indicating a decision to purchase the lightceutical clinical code is selected in the pop-up window, and performs a payment for a purchase of the lightceutical clinical code or the number of times that the lightceutical clinical code is usable in conjunction with a financial payment server; and operating a light therapy device in which, when it is determined that the lightceutical clinical code has been purchased or the number of times that the lightceutical clinical code is usable has not been exhausted in the determining of whether the lightceutical clinical code is owned or after the payment for the purchase of the lightceutical clinical code or the number of times that the lightceutical clinical code is usable is completed in the purchasing of the lightceutical clinical code, the information providing server reads the lightceutical clinical code from an information providing server DB and sends the read lightceutical clinical code to the smart communication device, and the smart communication device sends the received lightceutical clinical code to the light therapy device or generates a light therapy device control signal in accordance with the lightceutical clinical code and sends the generated light therapy device control signal to the light therapy device to operate the light therapy device.

The operation method may further include, between the purchasing of the lightceutical clinical code and the operating of the light therapy device, storing a response to a self-diagnosis questionnaire in which the smart communication device displays a self-diagnosis screen including questionnaire items related to a drug dose of a certain disease and sends a response to the self-diagnosis questionnaire input by the user via the self-diagnosis screen to the information providing server, and the information providing server stores the response to the self-diagnosis questionnaire in the information providing server DB.

The operation method may further include, after the operating of the light therapy device, storing a response to a therapy result questionnaire in which the smart communication device displays a therapy result input screen including questionnaire items related to a degree of pain and sends a response to the therapy result questionnaire input by the user via the therapy result input screen to the information providing server, and the information providing server stores the response to the therapy result questionnaire in the information providing server DB.

The operation method may further include outputting a therapy result in which, after a response is made to the therapy result questionnaire, the smart communication device statistically processes the response to the therapy result questionnaire or the response to the self-diagnosis questionnaire stored in the information providing server DB and displays the responses in weeks, months, and years.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
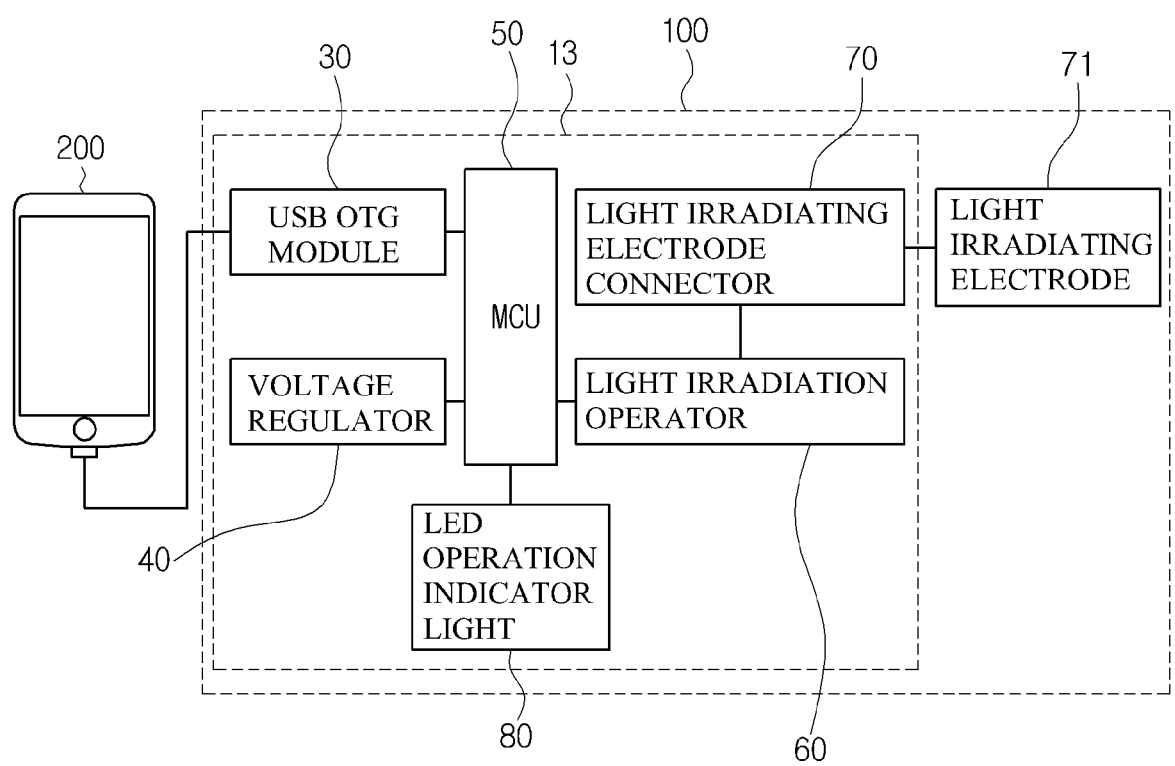
FIG. 1 is a view for describing a configuration of a low level light therapy device.
Figure 2:
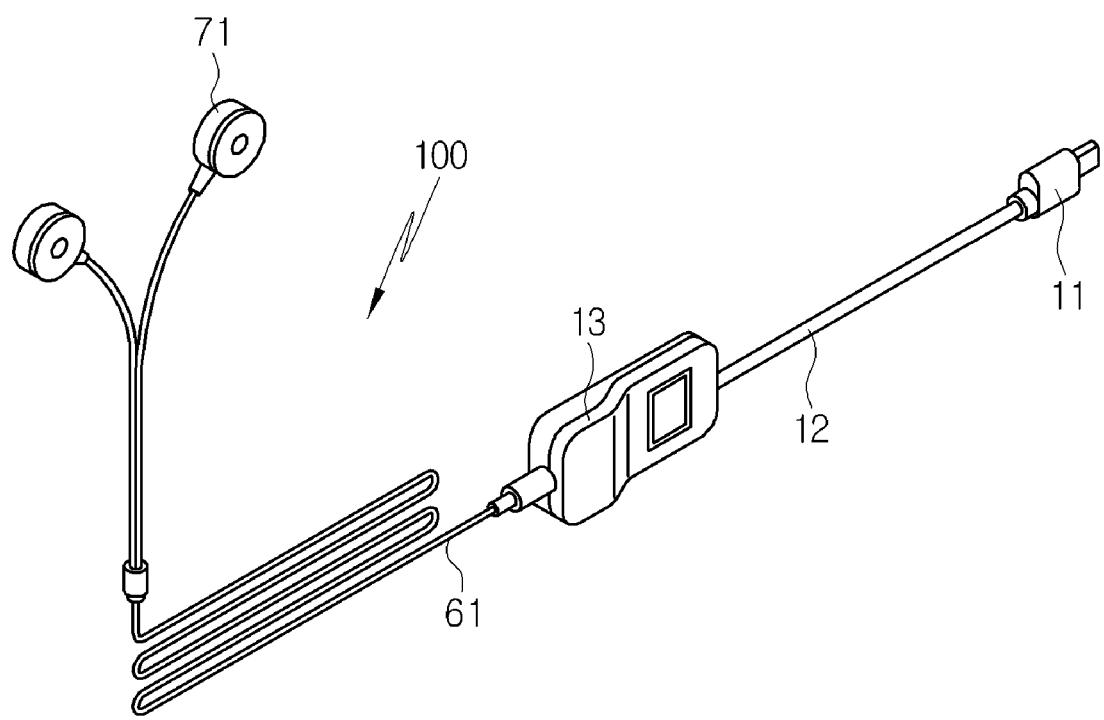
FIG. 2 illustrates an example of the low level light therapy device.

The present disclosure relates to a system for providing a smart communication device-based light therapy service in which, when a payment for purchasing a lightceutical clinical code including a wavelength of light, an intensity of light, an irradiation time of light, and an irradiation pattern of light is completed in conjunction with a financial payment server in a smart communication device, the smart communication device receives the lightceutical clinical code from an information providing server and sends the received lightceutical clinical code to a light therapy device or generates a light therapy device control signal in accordance with the lightceutical clinical code and sends the generated light therapy device control signal to the light therapy device, and the light therapy device is operated in accordance with the received lightceutical clinical code or light therapy device control signal.

An operation method of the system for providing a smart communication device-based light therapy service includes, at least, determining whether a lightceutical clinical code is owned, purchasing a lightceutical clinical code, storing a response to a self-diagnosis questionnaire, operating a light therapy device, storing a response to a therapy result questionnaire, and outputting a therapy result.

In the determining of whether the lightceutical clinical code is owned, the smart communication device determines whether a user has purchased and owns a lightceutical clinical code of a symptom or disease selected by the user via a disease selection screen or a symptom selection screen and determines whether a number of times that the lightceutical clinical code is usable has been exhausted.

In the purchasing of the lightceutical clinical code, when it is determined that the lightceutical clinical code has not been purchased or the number of times that the lightceutical clinical code is usable has been exhausted in the determining of whether the lightceutical clinical code is owned, the smart communication device displays a notification that the lightceutical clinical code has not already been purchased or the number of times that the lightceutical clinical code is usable has been exhausted and a pop-up window that asks whether to purchase the lightceutical clinical code, outputs a purchase screen when a switch indicating a decision to purchase the lightceutical clinical code is selected in the pop-up window, and performs a payment for a purchase of the lightceutical clinical code or the number of times that the lightceutical clinical code is usable in conjunction with a financial payment server.

In the storing of the response to the self-diagnosis questionnaire, when it is determined that the lightceutical clinical code has been purchased or the number of times that the lightceutical clinical code is usable has not been exhausted in the determining of whether the lightceutical clinical code is owned or after the payment for the purchase of the lightceutical clinical code or the number of times that the lightceutical clinical code is usable is completed in the purchasing of the lightceutical clinical code, the smart communication device displays a self-diagnosis screen including questionnaire items related to a drug dose of a selected disease and sends a response to the self-diagnosis questionnaire input by the user via the self-diagnosis screen to the information providing server, and the information providing server stores the response to the self-diagnosis questionnaire in the information providing server DB.

After the storing of the response to the self-diagnosis questionnaire, in the operating of the light therapy device, the information providing server reads the lightceutical clinical code from the information providing server DB and sends the read lightceutical clinical code to the smart communication device, and the smart communication device sends the received lightceutical clinical code to the light therapy device or generates a light therapy device control signal in accordance with the lightceutical clinical code and sends the generated light therapy device control signal to the light therapy device to operate the light therapy device.

After the operating of the light therapy device, in the storing of the response to the therapy result questionnaire, the smart communication device displays a therapy result input screen including questionnaire items related to a degree of pain and sends a response to the therapy result questionnaire input by the user via the therapy result input screen to the information providing server, and the information providing server stores the response to the therapy result questionnaire in the information providing server DB.

After a response is made to the therapy result questionnaire, in the outputting of the therapy result, the smart communication device statistically processes the response to the therapy result questionnaire or the response to the self-diagnosis questionnaire stored in the information providing server DB and displays the responses in weeks, months, and years.

Hereinafter, the present disclosure will be described in more detail with reference to the accompanying drawings.

Figure 3:
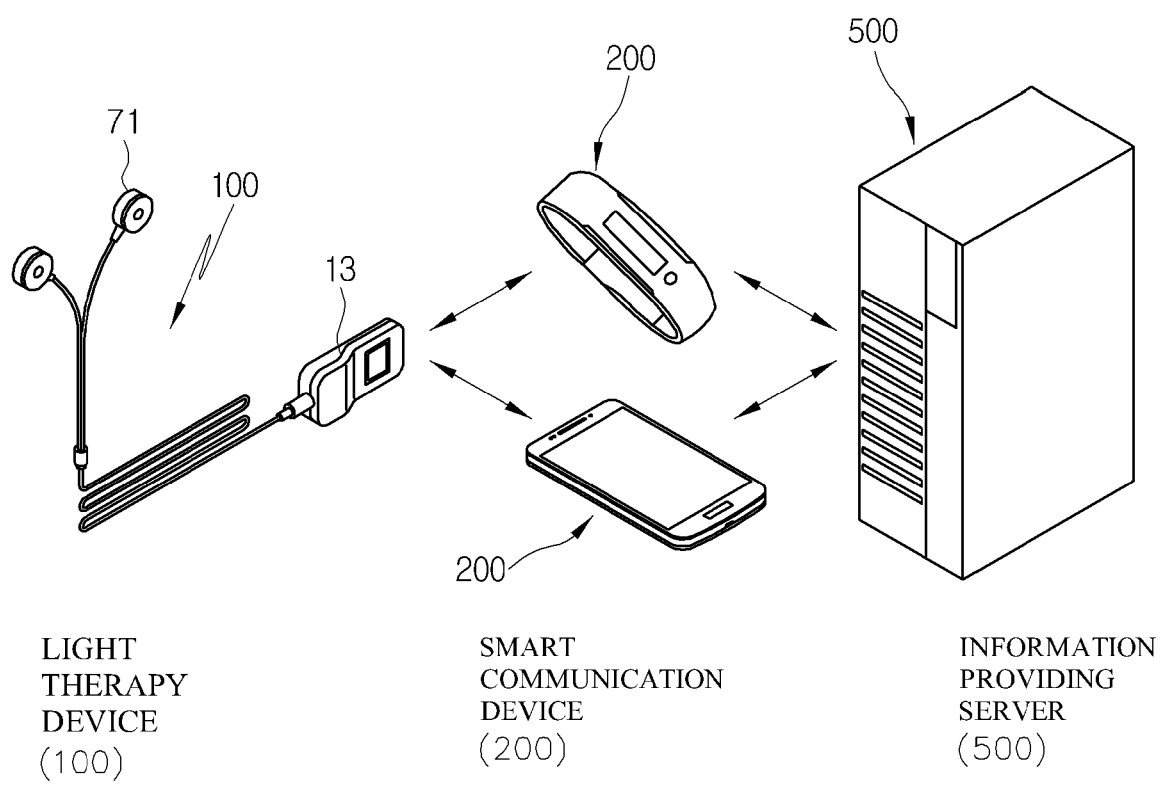
FIG. 3 is a schematic diagram for schematically describing a system for providing a smart communication device-based light therapy service according to the present disclosure.
Figure 4:
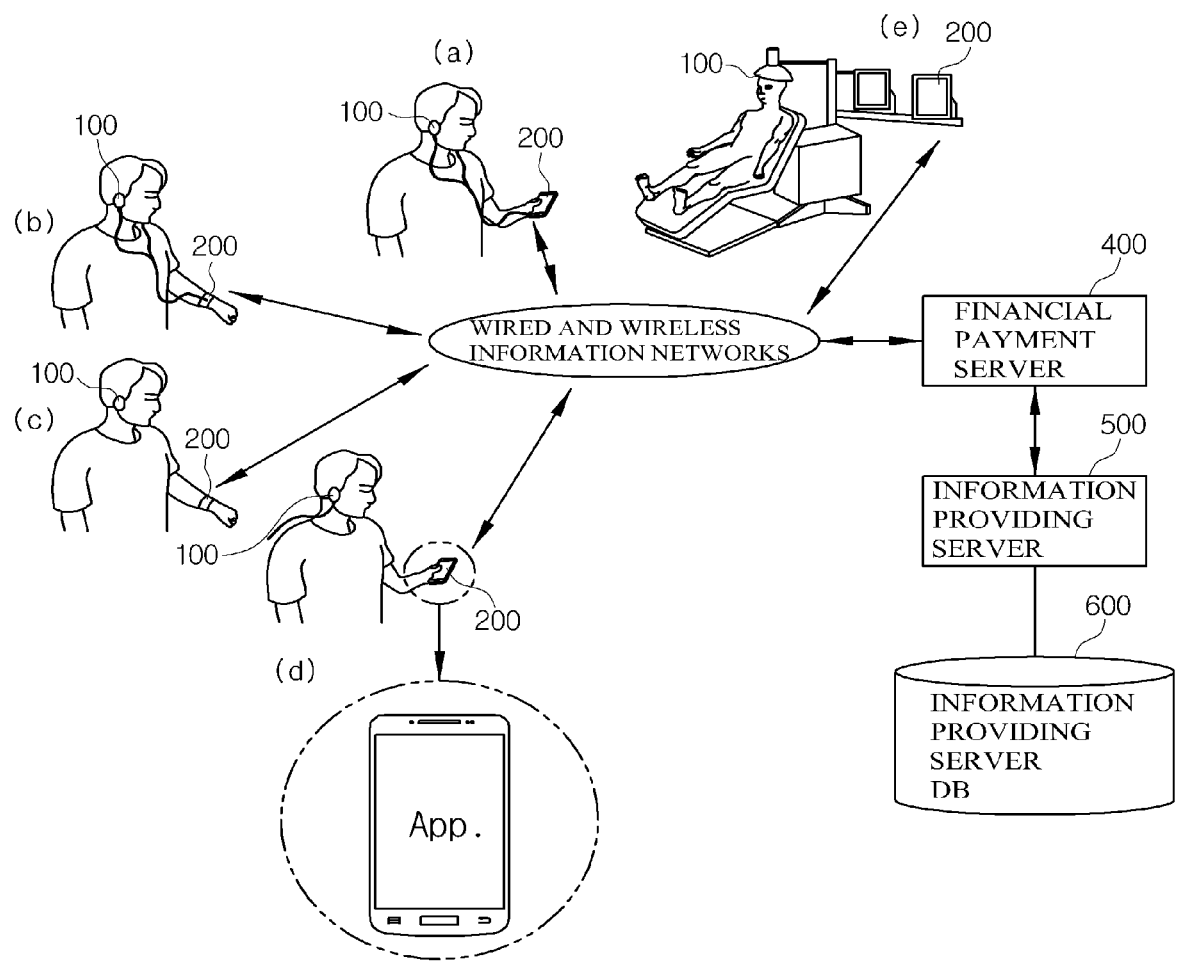
FIG. 4 is a schematic view for describing various embodiments to which the system for providing a smart communication device-based light therapy service according to the present disclosure is applied.

FIG. 3 is a schematic diagram for schematically describing a system for providing a smart communication device-based light therapy service according to the present disclosure, and FIG. 4 is a schematic view for describing various embodiments to which the system for providing a smart communication device-based light therapy service according to the present disclosure is applied.

As illustrated in FIG. 3, the system for providing a light therapy service includes a light therapy device 100, a smart communication device 200, and an information providing server 500.

The light therapy device 100 is a low level light therapy device and includes a light irradiating electrode 71 and a light therapy device controller (a smartphone interface for light therapy) 13. The light therapy device controller 13 controls a light source of the light irradiating electrode 71 in accordance with a light therapy device control signal or lightceutical clinical code received from the smart communication device 200. Here, the light irradiating electrode 71 and the light therapy device controller 13 may be connected via a wire or wirelessly.

The light therapy device 100 uses any one of a three-color LED, an organic LED (OLED), a quantum dot LED (QLED), and an active matrix OLED (AMOLED) as a light source that emits low level light, and a wavelength of emitted light, an intensity of light, an irradiation time of light, an irradiation pattern of flight, and on/off of low level light therapy are controlled via a wire or wirelessly through a light therapy application of the smart communication device 200. Because a low level light therapy device has been described in the above descriptions of Korean Unexamined Patent Application Publication No. 10-2016-0099352 and Korean Unexamined Patent Application Publication No. 10-2016-0055082, detailed description thereof will be omitted.

Although the light therapy device 100 is configured such that the light irradiating electrode 71 is connected to the light therapy device controller 13 and the light irradiating electrode 71 is mounted on any part of the human body according to FIG. 3, embodiments of the present disclosure is not limited thereto. The light therapy device 100 may be configured such that the light irradiating electrode and the light therapy device controller are built in in any one of a headgear, a patch, a necklace, a bracelet, a watch, a belt, a wrist band, a glove, a waist support, a shirt, and underpants. Alternatively, the light therapy device 100 may include the light irradiating electrode and the light therapy device controller and may be configured to be capable of being attached to any one of a headgear, a patch, a necklace, a bracelet, a watch, a belt, a wrist band, a glove, a waist support, a shirt, and underpants. The light irradiating electrode may be adhered to or located in the vicinity of a certain spot of the human body.

The smart communication device 200 is a smart communication device in which a predetermined light therapy application program, i.e., a light therapy application, provided from the information providing server 500 is installed through user authentication. The smart communication device 200 sends information on a disease or symptom input by the user to the information providing server 500, and, when a user purchases a predetermined lightceutical clinical code presented from the information providing server 500, the smart communication device 200 receives the predetermined lightceutical clinical code from the information providing server 500, receives information on a light therapy method in accordance with the lightceutical clinical code, generates a light therapy device control signal in accordance with the received lightceutical clinical code, sends the generated light therapy device control signal to the light therapy device controller 13 of the light therapy device 100 or sends the lightceutical clinical code to the light therapy device controller 13 of the light therapy device 100, and displays the information on the light therapy method in accordance with the lightceutical clinical code.

The lightceutical clinical code may be in the form of a number or a combination of numbers and letters by encoding values of a wavelength of light, an intensity of light, an irradiation time of light, and an irradiation pattern of light. That is, the lightceutical clinical code is a control signal that includes a wavelength of light, an intensity of light, an irradiation time of light, and an irradiation pattern of light suitable for therapy of a disease or symptom selected by the user. In other words, the lightceutical clinical code may be a set of set values of a wavelength of light, an intensity of light, an irradiation time of light, and an irradiation pattern of light output from the light therapy device 100.

The smart communication device 200 may be a smartphone, a wrist-worn smartphone (smart watch), a laptop, an iPad, a personal computer, and the like. Preferably, the smart communication device 200 may be any one of a smartphone and a smart watch using any one of the Android operating system (OS), the Android Wear OS, the Android Open Source Project OS, the Apple iOS, the Tizen OS, the MS window OS, the BlackBerry OS, the FireFox OS, and MiUi Color OS as an OS. The smart communication device 200 has the light therapy application installed therein, and the light therapy device 100 and the information providing server 500 are connected via a wire or wirelessly using the light therapy application.

When the user purchases a lightceutical clinical code using the smart communication device 200, a payment may be made by the smart communication device 200 operating in conjunction with a financial payment server 400 and the information providing server 500. The information on the light therapy method in accordance with the lightceutical clinical code may be information in the form of sound, image, or moving picture. Also, the smart communication device 200 and the light therapy device 100 may be connected via a wire or wirelessly.

In the present disclosure, the smart communication device 200 may connect to the information providing server 500 using the light therapy application, and the light therapy device 100 and user information of the user may be registered via a user interface (UI) screen of the smart communication device 200.

The smart communication device 200 may present several names of diseases or symptoms on the UI screen using the application to allow the user to select a disease name or symptom to be treated, provide information on a light therapy method related to the selected disease name or symptom to the user in the form of letters, images, photographs, or moving pictures, and allow the user to pay a predetermined service cost to purchase a lightceutical clinical code of the disease or symptom that the user wishes to treat or a number of times that the lightceutical clinical code is usable via the smart communication device. In some cases, the user may directly generate a lightceutical clinical code or change the lightceutical clinical code as needed via the smart communication device 200.

The smart communication device 200 generates a light therapy device control signal in accordance with a predetermined lightceutical clinical code that is purchased via the information providing server 500 or generated by the user through the low level light therapy application and sends the generated light therapy device control signal to the light therapy device 100 to perform low level light therapy.

The smart communication device 200 may allow the user to input states of his or her disease or symptom before and after light therapy via the UI screen through the light therapy application and store the input states in the information providing server 500. Also, the smart communication device 200 is linked to the information providing server 500 and displays a therapy result related to the user's disease or symptom before and after the light therapy to allow the user to check the therapy result in graphs or numerical values on a weekly basis, a monthly basis, and a yearly basis.

When the user purchases a lightceutical clinical code via the smart communication device 200, the financial payment server 400 linked to the smart communication device 200 is a server for making a payment. That is, the financial payment server 400 is a server required for the user to pay for a service cost for purchasing a lightceutical clinical code and a number of times of therapy using the lightceutical clinical code suitable for therapy of a disease or symptom selected by connecting to the information providing server 500 using the low level light therapy application via the smart communication device 200. The financial payment server 400 may use a self-authentication technology using a financial transaction certification of an individual, a financial payment server managed by a financial institution for a charged service, or a mobile payment service (for example, Google Pay, Samsung Pay, Kakao Pay, Naver Pay, Payco, SSG Pay, L-Pay, Apple Pay, and Ali Pay). Because these are widely known technologies, one of ordinary skill in the art should be able to easily understand technologies linked to the above technologies and implement the technologies in various ways without description of the technologies.

The information providing server 500 receives personal information such as a device number of the light therapy device 100, a password, the user's gender, the user's age, and the user's skin color from the smart communication device 200 and stores the received personal information in a customer information DB. When the low level light therapy application is executed in the smart communication device 200, several diseases or symptoms are presented on the UI screen, and the user selects a disease or symptom to be treated.

The information providing server 500 determines whether a lightceutical clinical code related to the disease or symptom selected by the user has been already purchased, and, when the number of times that the lightceutical clinical code is usable has been exceeded and exhausted or the lightceutical clinical code has not been purchased, the information providing server 500 notifies the smart communication device 200 of the situation, and the smart communication device 200 notifies the user of the situation by displaying using letters, presents the UI screen through which the user can purchase the lightceutical clinical code, and allows the user to select a predetermined lightceutical clinical code and a number of times of therapy using the lightceutical clinical code and purchase the lightceutical clinical code and the number of times of therapy using the lightceutical clinical code by making a payment in conjunction with the financial payment server 400.

When the user purchases the lightceutical clinical code and the number of times of therapy using the lightceutical clinical code related to the disease or symptom selected by himself or herself, the information providing server 500 reads the lightceutical clinical code from an information providing server DB 600 in accordance with information on the disease or symptom received from the smart communication device 200 and generates the lightceutical clinical code, reads information on a therapy method related to the disease or symptom of the user and internationally standardized disease questionnaire related to the disease or symptom from the information providing server DB 600, and sends the information on the therapy method and the disease questionnaire as well as the generated lightceutical clinical code to the smart communication device 200. The smart communication device 200 generates a light therapy device control signal in accordance with the received lightceutical clinical code and sends the generated light therapy device control signal to the light therapy device 100, causing the light therapy device 100 to operate in accordance with the light therapy device control signal. Also, for self-diagnosis before therapy, the received disease questionnaire is displayed on the smart communication device 200 for the user to record his or her state before therapy, the smart communication device 200 sends this (that is, a response of the user to the questionnaire) to the information providing server 500 so that the response is stored in the information providing server DB 600, and the smart communication device 200 outputs the information on the therapy method to allow the user to perform therapy while referring to the information on the therapy method. Here, the information on the therapy method includes a suitable therapy time per each therapy, an effective therapy time, a therapy period, a spot on which the light irradiating electrode (light irradiating probe) is mounted, and the like.

The information providing server 500 stores, in the information providing server DB 600, personal information such as a device number of the light therapy device, a password, the user's gender, the user's age, the user's skin color, a name of a disease, and a name of a symptom input by the user via the smart communication device 200, stores the user's response to the self-diagnosis questionnaire input via the self-diagnosis screen on the smart communication device 200 before the treatment (that is, a state of a disease or symptom of the user before the light therapy), and stores the user's response to the therapy result questionnaire input via the therapy result input screen on the smart communication device 200 after the treatment (that is, a state of the disease or symptom of the user after the light therapy (therapy effect)).

The therapy result input screen includes multiple questionnaire items. Here, at least a questionnaire item related to a degree of pain of the disease selected by the user (a degree of pain felt by the user) is include in the questionnaire items.

The information providing server DB 600 stores lightceutical clinical codes including a wavelength of light, an intensity of light, an irradiation time of light, and an irradiation pattern of light suitable for each disease or symptom that may be treated by low level light therapy, therapy methods for each of the diseases or symptoms including a position to which the light irradiating electrode is to be attached, internationally standardized self-diagnosis (disease) questionnaires and therapy result (disease) questionnaires, and the like. Also, the information providing server DB 600 encodes and stores the device number and password of the light therapy device and the user information (e.g., gender, age, skin color) received via the information providing server 500 and stores the use's response to the self-diagnosis (disease) questionnaire and response to the therapy result (disease) questionnaire received via the smart communication device 200 for each user and by date.

When the information providing server 500 receives a request to check the light therapy result from the smart communication device 200, the information providing server 500 sends the result stored for each device number of the light therapy device, disease or symptom, and by date in the information providing server DB 600 to the smart communication device 200 and allows the user to check the result on a weekly basis, a monthly basis, and a yearly basis.

In the present disclosure, any one of a get method, a post method, and other latest information transmission methods is used to transmit data between the smart communication device 200 and the information providing server 500. Data is transmitted therebetween by being encoded using any one of an application programming interface (API) method, a Plug-In method, and other latest encoding methods.

In the present disclosure, the UI language of the light therapy application is one of the languages registered in the United Nations (UN).

In the present disclosure, the smart communication device 200 and the low level light therapy device 100 are wirelessly connected using one of Zigbee, Bluetooth, near-field communication (NFC), wireless fidelity (Wi-Fi), and radio frequency (RF). When the smart communication device 200 and the light therapy device 100 are connected via a wire, the smart communication device 200 and the light therapy device 100 are connected using a USB terminal, an iPhone terminal, Recommended Standard-232C (RS232C), Inter-integrated circuit (I2C), or serial peripheral interface (SPI).

FIG. 4 illustrates a case in which the light therapy device 100 is worn in the ear, but embodiments of the present disclosure is not limited thereto. The light therapy device 100 may be worn on any other part of the user's body including the earlobe, the earhole, the face, the stomach (abdomen), the back, the arms, and the legs.

FIG. 4(*a*) illustrates a case in which a smartphone is used as the smart communication device 200 and the light therapy device 100 and the smartphone are connected via a wire; FIG. 4(*b*) illustrates a case in which a wrist-worn smartphone is used as the smart communication device 200 and the light therapy device 100 and the wrist-worn smartphone are connected via a wire; FIG. 4(*c*) illustrates a case in which a wrist-worn smartphone is used as the smart communication device 200 and the light therapy device 100 and the wrist-worn smartphone are wirelessly connected; FIG. 4(*d*) illustrates a case in which a smartphone is used as the smart communication device 200 and the light therapy device 100 and the smartphone are wirelessly connected; and FIG. 4(*e*) illustrates a case in which a personal computer is used as the smart communication device 200 and the light therapy device 100 and the personal computer are connected via a wire.

In the present disclosure, an application program, i.e., the low level light therapy device application, installed in the smart communication device 200 includes a function of connecting the smart communication device 200 and the low level light therapy device 100 via a wire or wirelessly, a function of connecting to the information providing server 500 by inputting the device number and the password of the low level light therapy device 100 in the smart communication device 200 and registering the low level light therapy device 100 as a user device via the UI screen of the smart communication device 200 while the smart communication device 200 is connected to the information providing server 500, a function of registering user information such as gender, age, and skin color, a function of presenting several names of diseases and symptoms to the user and allowing the user to select a disease or symptom to be treated, a function of providing information on a therapy method for the disease or symptom selected by the user in the form of letters, images, photographs, or moving pictures, a function of allowing the user to input a current state of his or her disease or symptom through an internationally standardized disease questionnaire related to the disease or symptom before therapy, i.e., a self-diagnosis questionnaire on the self-diagnosis screen, a function of allowing the user to change the lightceutical clinical code as needed, a function of fallowing the user to send a purchased lightceutical clinical code to the low level light therapy device 100 via a wire or wirelessly to perform the low level light therapy, a function of preventing selection of an unpurchased lightceutical clinical code or operation of a light therapy device related to a certain disease or symptom other than selection of the lightceutical clinical code related to a certain disease or symptom purchased by the user, a function of presenting a number of times of therapy capable of treating the disease or symptom purchased by the user and, when the number of times that the lightceutical clinical code is usable for therapy is displayed as "0," preventing the lightceutical clinical code from being sent to the light therapy device 100, a function of allowing the user to input a current state of his or her disease or symptom through an internationally standardized disease questionnaire related to the disease or symptom after light therapy, i.e., therapy result questionnaire on the therapy result input screen, a function of allowing the user to check the therapy result by comparing data related to his or her states of the disease or symptom before and after the low level light therapy on a weekly basis, a monthly basis, and a yearly basis, a function of allowing the user to pay a service cost via the smart communication device 200 to purchase a lightceutical clinical code and a number of times of therapy using the lightceutical clinical code required for treating the disease or symptom that the user wishes to treat, a function of presenting a number of times of therapy capable of treating the disease or symptom purchased by the user and, when the number of times that the lightceutical clinical code is usable for therapy becomes "0," informing the user with letters that the number of times that the lightceutical clinical code is usable for therapy has to be re-purchased to treat the disease or symptom and presenting the UI screen through which the user can purchase the number of times that the lightceutical clinical code is usable for therapy to allow the user to re-purchase the number of times that the lightceutical clinical code is usable for therapy, and a function sending data input by the user for the low level light therapy to the information providing server 500 using wired and wireless information networks to store the data in the information providing server DB 600.

Figure 5:
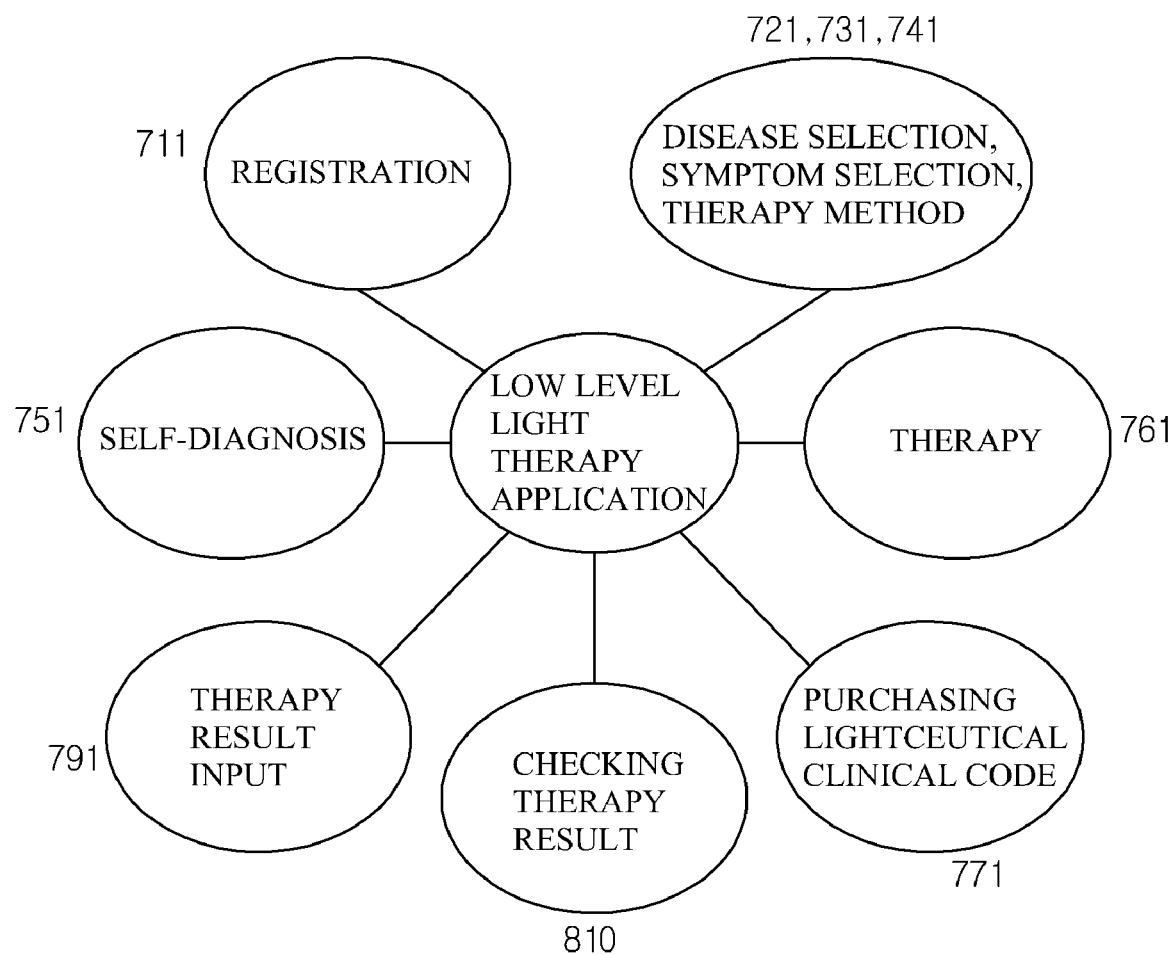
FIG. 5 is a block diagram of an application for a low level light therapy device of a system and method for providing a smart communication device-based low level light therapy service according to the present disclosure.

FIG. 5 is a block diagram of an application for a low level light therapy device of a system and method for providing a smart communication device-based low level light therapy service according to the present disclosure.

The light therapy device application allows registration of a light therapy device and user information, disease selection and information provision, self-diagnosis, low level light therapy, an input of a state after therapy, checking a therapy result, and purchasing a lightceutical clinical code. That is, the light therapy device application includes a registration screen, a disease selection screen, a symptom selection screen, a therapy method screen, a therapy screen, a lightceutical clinical code purchase screen, a therapy result checking screen, a therapy result input screen, a self-diagnosis screen, and the like.

Figure 6:
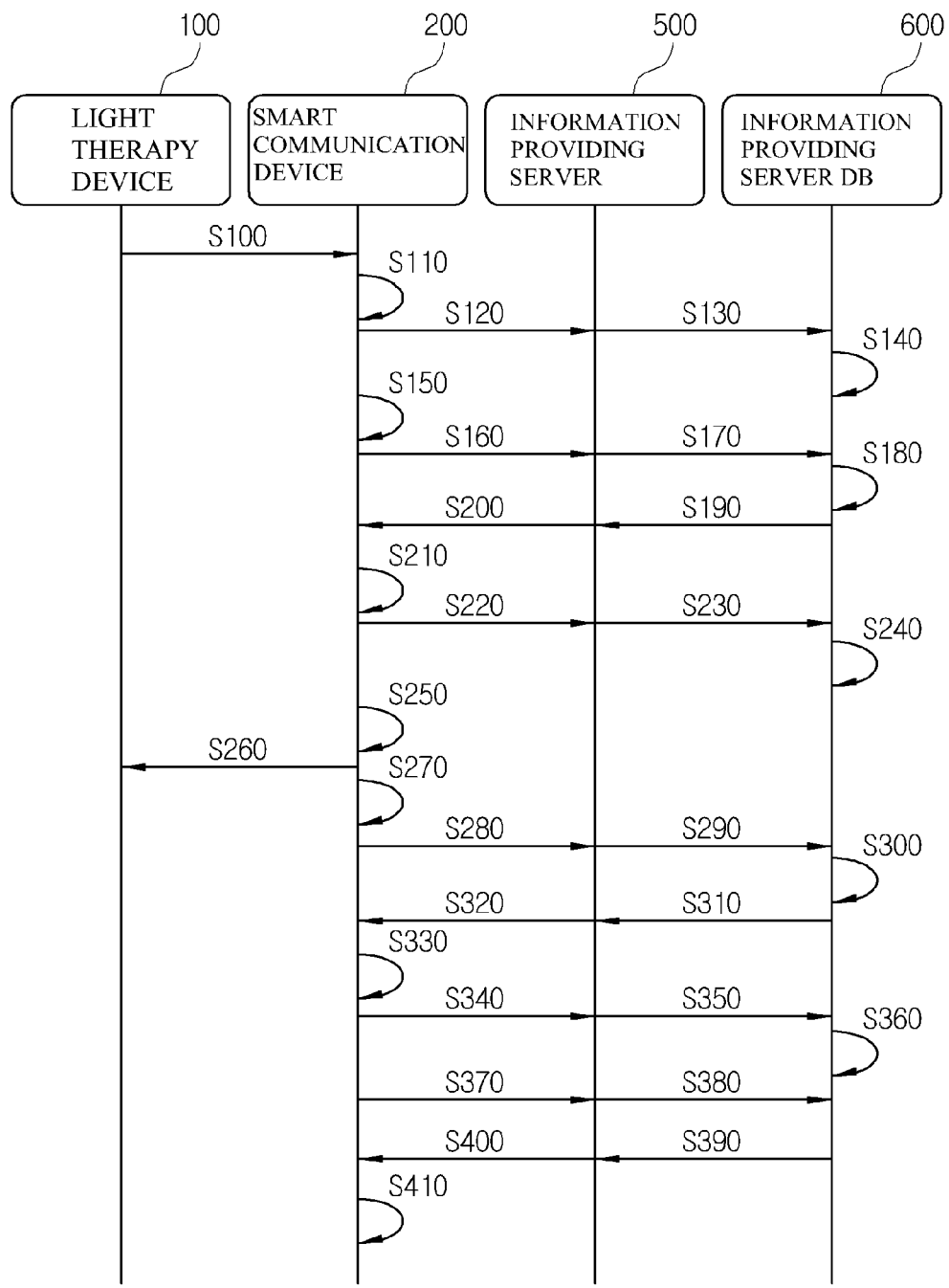
FIG. 6 is a therapy performing flowchart of a new user using the system and method for providing a light therapy service according to the present disclosure.

FIG. 6 is a therapy performing flowchart of a new user using the system and method for providing a smart communication device-based low level light therapy service according to the present disclosure.

In pairing with the smart communication device, the light therapy device 100 is connected to the smart communication device 200 via a wire or wirelessly (S100).

After the smart communication device 200 and the low level light therapy device 100 are connected via a wire or wirelessly in the pairing with the smart communication device, in registering, a registration button 702 on an initial screen 701 of the smart communication device 200 is selected to load the registration screen, the user inputs a device number (e.g., a serial number) of the light therapy device 100 owned by the user, a password (e.g., a membership password), and user information (e.g., gender, age, skin color) via the registration screen on the smart communication device 200 (S110), the smart communication device 200 encodes the input information and sends the encoded information to the information providing server 500 (S120), the information providing server 500 sends the received information to the information providing server DB 600 (S130), and the sent information is stored as customer-related information in the information providing server DB 600 (S140). In some cases, in Step S120, the information providing server 500 may authenticate user information (using a certificate and the like) and store the authenticated user information in the information providing server DB 600.

Here, when the smart communication device 200 and the low level light therapy device 100 are connected via a wire, the low level light therapy device application is automatically run. When the smart communication device 200 and the low level light therapy device 100 are wirelessly connected, the smart communication device 200 is connected to the low level light therapy device 100 owned by the user via wireless communication (e.g., Bluetooth) after the low level light therapy device application is run.

After input of the user information via the smart communication device 200 is completed and the user information is registered in the registering, in selecting a disease or symptom, the user selects a name of a disease or a symptom to be treated via a disease selection screen 721 or a symptom selection screen 731 of the smart communication device 200 (S150), the symptom information or disease information selected by the user is sent from the smart communication device 200 to the information providing server 500 (S160), the information providing server 500 sends the information to the information providing server DB 600 (S170), and the information is stored as additional customer-related information in the information providing server DB 600 (S180).

In receiving therapy method information, the information providing server 500 reads self-diagnosis questionnaire in addition to information required for therapy (therapy method information) from the information providing server DB 600 in accordance with the information on the name of the disease or symptom selected in the selecting of the disease or symptom (S190), and sends the questionnaire and the information to the smart communication device 200 to display the information on a screen of the smart communication device (S200).

Here, the information required for therapy, i.e., therapy method information, may be information such as an electrode attaching position of the low level light therapy device 100, a therapy time and number of times of therapy per day, a method of using the low level light therapy device 100, and precautions indicated using one of letters, images, photographs, and moving pictures. The self-diagnosis questionnaire is a questionnaire used before and after therapy and refers to an internationally standardized disease questionnaire related to a disease or symptom for self-diagnosis.

After the user checks information required for low level light therapy (i.e., therapy method information) in accordance with the information required for therapy (therapy method information) and the self-diagnosis questionnaire displayed on the smart communication device 200 in the receiving of the therapy method information, in storing a response to a self-diagnosis questionnaire, the user performs self-diagnosis in which the user inputs a current state of his or her disease or symptom (S210), and when the self-diagnosis is completed, information input to the smart communication device 200, i.e., the response to the self-diagnosis questionnaire, is encoded and sent to the information providing server 500 via wired and wireless information networks 300 (S220), the information providing server 500 sends the information to the information providing server DB 600 (S230), and the sent self-diagnosis information is stored as additional customer-related information in the information providing server DB 600 (S240).

Although not illustrated in FIG. 6, the flowchart may further include purchasing a lightceutical clinical code after the selecting of the disease or symptom (S180) or after the storing of the response to the self-diagnosis questionnaire (S240).

In the purchasing of the lightceutical clinical code, the smart communication device 200 or the information providing server 500 determines whether the user has already purchased and owns the lightceutical clinical code corresponding to the disease or symptom selected by the user in the selecting of the disease or symptom and whether the number of times that the lightceutical clinical code is usable has already been exhausted, and when the lightceutical clinical code has not been purchased or the number of times that the lightceutical clinical code is usable has been exhausted, a screen for purchasing the lightceutical clinical code is displayed on the smart communication device 200 to allow the user to purchase the lightceutical clinical code.

After the user completes the self-diagnosis process by responding to the self-diagnosis questionnaire using the smart communication device 200 in the storing of the response to the self-diagnosis questionnaire, in operating a light therapy device, a therapy screen (i.e., a therapy performing screen) is presented to the user (S250), and the user performs the low level light therapy using the therapy screen (i.e., the therapy performing screen). Here, the lightceutical clinical code is automatically sent from the smart communication device 200 to the light therapy device 100 and the light therapy device 100 is operated in accordance with the lightceutical clinical code, or a light therapy device control signal is generated in accordance with the lightceutical clinical code sent from the smart communication device 200, the generated light therapy device control signal is sent to the light therapy device 100, and the light therapy device 100 is operated in accordance with the light therapy device control signal such that the therapy is performed by light for therapy being irradiated from the light therapy device 100 (S260).

Here, the lightceutical clinical code is encoded information including a wavelength of light, an intensity of light, an irradiation time of light, and an irradiation pattern of light set on the basis of the user's gender, age, and skin color input when the user purchases the lightceutical clinical code for treating a disease or symptom that the user wishes to treat.

After a light irradiation stop button is forcibly selected or a set therapy time ends during therapy in the operating of the light therapy device, in ending an operation of the light therapy device, the low level light therapy is automatically ended, the fact that the low level light therapy is ended is sent to the smart communication device 200, and after the therapy is ended, the lightceutical clinical code stored in the low level light therapy device 100 or the smart communication device 200 is cleared (initialized), and the number of times that the purchased lightceutical clinical code is usable stored in the smart communication device 200 is also updated by a predetermined number of times of therapy performed using the lightceutical clinical code (for example, four) being subtracted therefrom such that a value resulting from subtracting the number of times of therapy performed using the lightceutical clinical code (for example, four) from the number of times that the purchased lightceutical clinical code is usable is displayed on the therapy screen (S270).

After the low level light therapy using the light therapy device 100 is ended in the ending of the operation of the light therapy device, in storing therapy end information, therapy end information, i.e., an actual number of times of therapy (or therapy time interval information) and the remaining number of times that the lightceutical clinical code is usable, in addition to a therapy end notification signal, which is a signal notifying of the end of the therapy, is sent from the smart communication device 200 to the information providing server 500 (S280), the information providing server 500 sends the received signal and information to the information providing server DB 600 (S290), and the sent therapy end information is stored as additional customer information in the information providing server DB 600 (S300).

After the information providing server 500 receives the therapy end notification signal in the storing of the therapy end information, in storing a response to a therapy result questionnaire, the information providing server 500 reads a therapy result questionnaire, which is an internationally standardized disease questionnaire, from the information providing server DB 600 (S310) and sends the read therapy result questionnaire to the smart communication device 200 (S320). When the user selects a therapy result button and a result input button via the smart communication device 200 after therapy, the smart communication device 200 displays the therapy result questionnaire, and when the user inputs a response to the therapy result questionnaire, the smart communication device 200 sends the response to the therapy result questionnaire to the information providing server 500 (S340), the information providing server 500 sends the received response to the therapy result questionnaire to the information providing server DB 600 (S350), and the received response to the therapy result questionnaire is stored as additional customer information in the information providing server DB 600 (S360).

That is, the therapy result button is generated on the therapy screen of the smart communication device 200 when the therapy is ended, and the smart communication device 200 displays a therapy result main screen when the user selects the therapy result button after therapy. A calendar marked with days on which therapy is performed, days on which therapy is not performed, and today, the therapy result input button, and the therapy result checking button are presented on the therapy result main screen. When the user selects the therapy result input button and inputs a state of his or her disease or symptom after therapy for the disease or symptom in accordance with the therapy result questionnaire via the therapy result input screen, the response to the therapy result questionnaire is sent to the information providing server 500 via the wired and wireless information networks 300 and is stored as additional customer information in the information providing server DB 600.

After storage of the response to the therapy result questionnaire is completed in the storing of the response to the therapy result questionnaire, and the user selects the therapy result checking button to check his or her states before and after therapy, in outputting a therapy result, the smart communication device 200 displays the therapy result checking screen, and when the user selects a predetermined period (e.g., a week, a month, a year) button indicating a period of which the user wants to check the result via the therapy result checking screen, the smart communication device 200 sends a therapy result checking request signal for a predetermined period to the information providing server 500 (S370), the information providing server 500 sends the received signal to the information providing server DB 600 (S380), the information providing server 500 receives a therapy result of the predetermined period (that is, states of the user before and after therapy) from the information providing server DB 600 (S390) and sends the received therapy result to the smart communication device 200 (S400), and the smart communication device 200 displays the therapy result of the predetermined period by showing the therapy result related to the disease or symptom in graphs or numerical values on a weekly basis, a monthly basis, and a yearly basis to allow the user to check the therapy effect (S410).

The therapy result received from the information providing server DB 600 is statistical data related to the user's response to the self-diagnosis questionnaire input before therapy and the user's response to the therapy result questionnaire input after the therapy.

Figure 7:
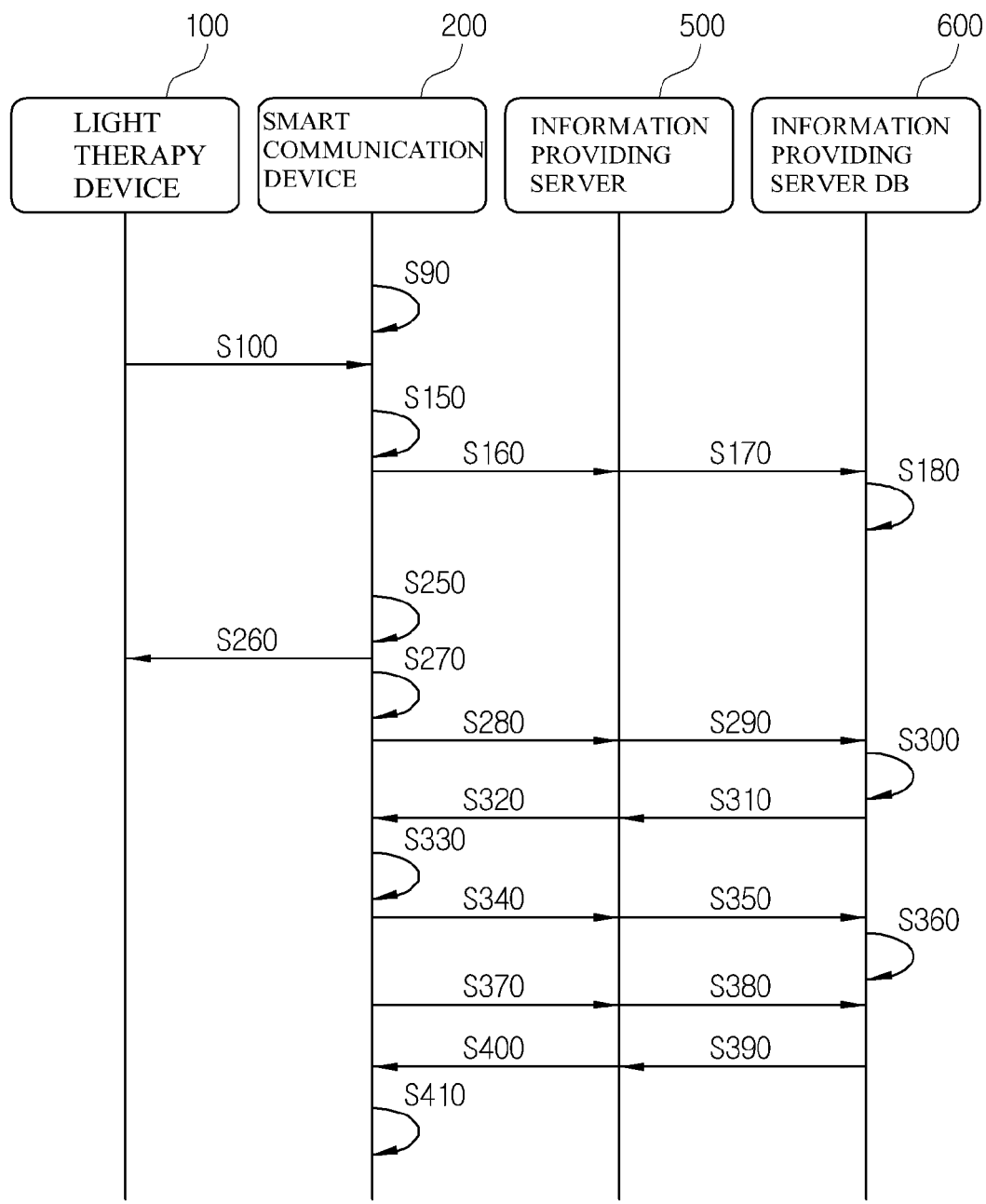
FIG. 7 is a therapy performing flowchart of a registered user using the system and method for providing a light therapy service according to the present disclosure.

FIG. 7 is a therapy performing flowchart of a registered user using the system and method for providing a smart communication device-based low level light therapy service according to the present disclosure.

In pairing with the smart communication device, when the user has selected an alarm function in the smart communication device 200, and an alarm rings at a selected time (S90), the user connects the light therapy device 100 owned by himself or herself to the smart communication device 200 via a wire or wirelessly (S100). When the user has not selected the alarm function, the user connects the light therapy device 100 owned by himself or herself to the smart communication device 200 via a wire or wirelessly (S100).

Here, when the smart communication device 200 and the low level light therapy device 100 are connected via a wire, the low level light therapy device app is automatically run. When the smart communication device 200 and the low level light therapy device 100 are wirelessly connected, the smart communication device 200 is connected to the light therapy device 100 owned by the user via wireless communication (e.g., Bluetooth) after the light therapy device application is run.

After connection of the light therapy device 100 owned by the user to the smart communication device 200 is completed in the pairing with the smart communication device, in selecting a disease or symptom, the user selects a name of a disease or a symptom to be treated via the disease selection screen 721 or the symptom selection screen 731 of the smart communication device 200 (S150), the symptom information or disease information selected by the user is sent from the smart communication device 200 to the information providing server 500 (S160), the information providing server 500 sends the information to the information providing server DB 600 (S170), and the information is stored as additional customer-related information in the information providing server DB 600 (S180).

After the disease or symptom to be treated is selected in the selecting of the disease or symptom, in operating a light therapy device, a therapy screen (i.e., a therapy performing screen) is displayed on the smart communication device 200 (S250), and the user performs the light therapy using the therapy screen. Here, the lightceutical clinical code is automatically sent from the smart communication device 200 to the light therapy device 100 and the light therapy device 100 is operated in accordance with the lightceutical clinical code, or a light therapy device control signal is generated in accordance with the lightceutical clinical code sent from the smart communication device 200, the generated light therapy device control signal is sent to the light therapy device 100, and the light therapy device 100 is operated in accordance with the light therapy device control signal such that the therapy is performed by light for therapy being irradiated from the light therapy device 100 (S260).

After a light irradiation stop button is forcibly selected or a set therapy time ends during therapy in the operating of the light therapy device, in ending an operation of the light therapy device, the light therapy is automatically ended, the fact that the light therapy is ended is sent to the smart communication device 200, and after the therapy is ended, the lightceutical clinical code stored in the low level light therapy device 100 or the smart communication device 200 is cleared (initialized), and the number of times that the purchased lightceutical clinical code is usable stored in the smart communication device 200 is also updated by a predetermined number of times of therapy performed using the lightceutical clinical code (for example, four) being subtracted therefrom such that a value resulting from subtracting the number of times of therapy performed using the lightceutical clinical code (for example, four) from the number of times that the purchased lightceutical clinical code is usable is displayed on the therapy screen (S270).

After the low level light therapy using the light therapy device 100 is ended in the ending of the operation of the light therapy device, in storing therapy end information, therapy end information, i.e., an actual number of times of therapy (or therapy time interval information) and the remaining number of times that the lightceutical clinical code is usable, in addition to a therapy end notification signal, which is a signal notifying of the end of the therapy, is sent from the smart communication device 200 to the information providing server 500 (S280), the information providing server 500 sends the received signal and information to the information providing server DB 600 (S290), and the sent therapy end information is stored as additional customer information in the information providing server DB 600 (S300).

After the information providing server 500 receives the therapy end notification signal in the storing of the therapy end information, in storing a response to a therapy result questionnaire, the information providing server 500 reads a therapy result questionnaire from the information providing server DB 600 (S310) and sends the read therapy result questionnaire to the smart communication device 200 (S320). When the user selects a therapy result button and a result input button via the smart communication device 200 after therapy, the smart communication device 200 displays the therapy result questionnaire, and when the user inputs a response to the therapy result questionnaire, the smart communication device 200 sends the response to the therapy result questionnaire to the information providing server 500 (S340), the information providing server 500 sends the received response to the therapy result questionnaire to the information providing server DB 600 (S350), and the received response to the therapy result questionnaire is stored as additional customer information in the information providing server DB 600 (S360).

After storage of the response to the therapy result questionnaire is completed in the storing of the response to the therapy result questionnaire, and the user selects the therapy result checking button to check his or her states before and after therapy, in outputting a therapy result, the smart communication device 200 displays the therapy result checking screen, and when the user selects a predetermined period (e.g., a week, a month, a year) button indicating a period of which the user wants to check the result via the therapy result checking screen, the smart communication device 200 sends a therapy result checking request signal for a predetermined period to the information providing server 500 (S370), the information providing server 500 sends the received signal to the information providing server DB 600 (S380), the information providing server 500 receives a therapy result of the predetermined period (that is, states of the user before and after therapy) from the information providing server DB 600 (S390) and sends the received therapy result to the smart communication device 200 (S400), and the smart communication device 200 displays the therapy result of the predetermined period by showing the therapy result related to the disease or symptom in graphs or numerical values on a weekly basis, a monthly basis, and a yearly basis to allow the user to check the therapy effect (S410).

FIG. 6 is a therapy performing flowchart of a new user while FIG. 7 is a therapy performing flowchart of a registered user. The therapy performing flowchart of FIG. 7 is different from the therapy performing flowchart of FIG. 6 in that the user sets an alarm in the smart communication device 200 to end a therapy time and that storing a response to a self-diagnosis questionnaire that is performed before therapy is not included.

Figure 8:
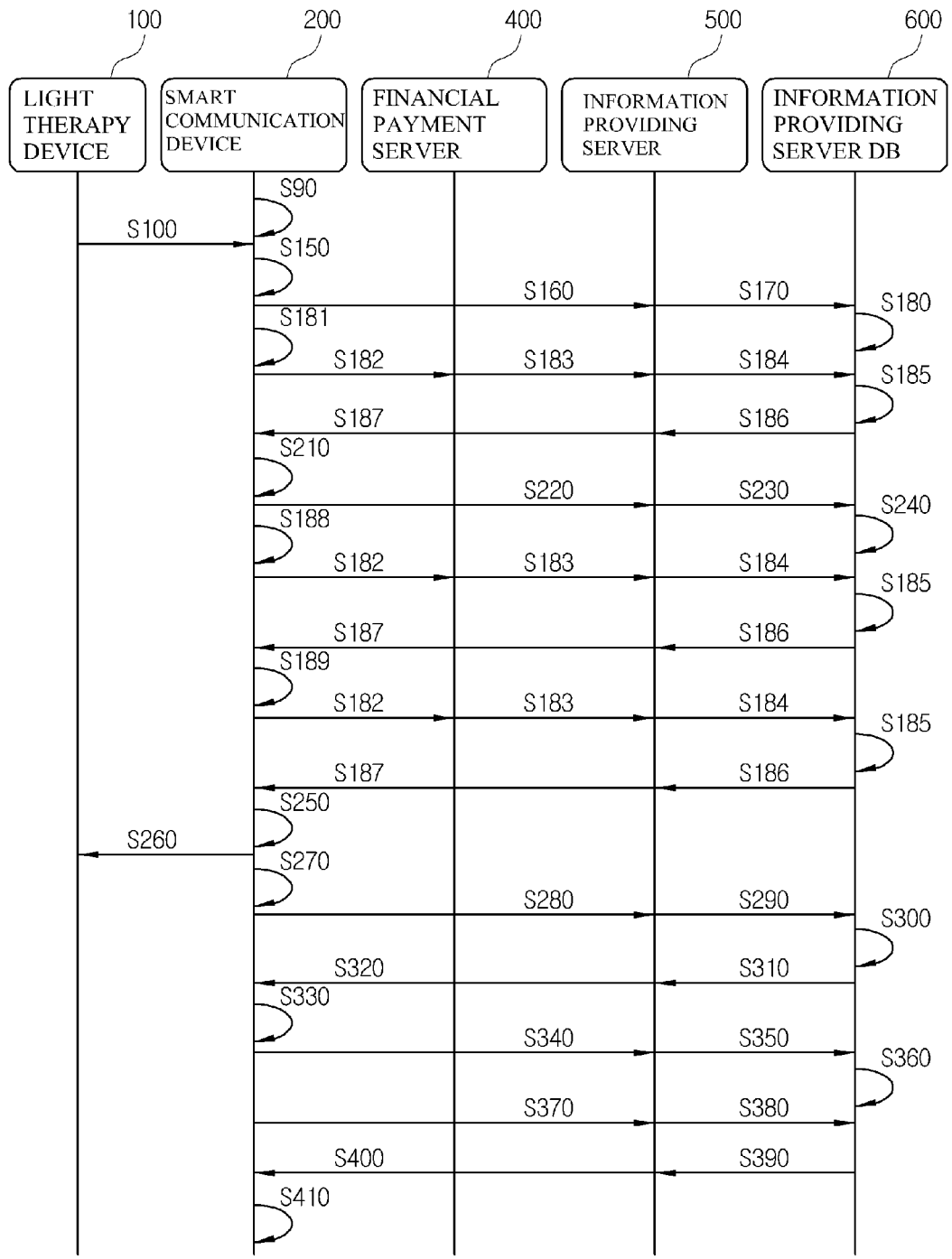
FIG. 8 is a therapy performing flowchart of the registered user through a purchase of a lightceutical clinical code, an additional purchase of the lightceutical clinical code, or an additional purchase of a number of times that the lightceutical clinical code is usable, using the system and method for providing a light therapy service according to the present disclosure.

FIG. 8 is a therapy performing flowchart of the registered user through an additional purchase of the lightceutical clinical code or an additional purchase of a number of times that the lightceutical clinical code is usable, using the system and method for providing a smart communication device-based low level light therapy service according to the present disclosure.

In pairing with the smart communication device, when the user has selected an alarm function in the smart communication device 200, and an alarm rings at a selected time (S90), the user connects the light therapy device 100 owned by himself or herself to the smart communication device 200 via a wire or wirelessly (S100). When the user has not selected the alarm function, the user connects (pairs) the light therapy device 100 owned by himself or herself to (with) the smart communication device 200 via a wire or wirelessly (S100).

Here, when the smart communication device 200 and the low level light therapy device 100 are connected via a wire, the low level light therapy device app is automatically run. When the smart communication device 200 and the low level light therapy device 100 are wirelessly connected, the smart communication device 200 is connected to the light therapy device 100 owned by the user via wireless communication (e.g., Bluetooth) after the light therapy device application is run.

After connection of the light therapy device 100 owned by the user to the smart communication device 200 is completed in the pairing with the smart communication device, in selecting a first disease or symptom, the user selects a name of a disease or a symptom to be treated via the disease selection screen 721 or the symptom selection screen 731 of the smart communication device 200 (S150), the symptom information or disease information selected by the user is sent from the smart communication device 200 to the information providing server 500 (S160), the information providing server 500 sends the information to the information providing server DB 600 (S170), and the information is stored as additional customer-related information in the information providing server DB 600 (S180).

In purchasing a first lightceutical clinical code, the smart communication device 200 or the information providing server 500 determines whether the user has already purchased and owns the lightceutical clinical code corresponding to the disease or symptom selected by the user in the selecting of the first disease or symptom and whether the number of times that the lightceutical clinical code is usable has already been exhausted, and when the lightceutical clinical code has not been purchased or the number of times that the lightceutical clinical code is usable has been exhausted, the user is informed of the fact that he or she needs to purchase the lightceutical clinical code using letters, the smart communication device 200 displays a screen for purchasing the lightceutical clinical code, which is the UI screen through which the user can purchase the lightceutical clinical code (S181), allows the user to select a number of times of therapy using the lightceutical clinical code related to the disease selected in the selecting of the first disease or symptom (that is, the number of times that the lightceutical clinical code is usable) via the screen for purchasing the lightceutical clinical code. A purchase cost is determined in accordance with a name of the disease and the number of times that the lightceutical clinical code is usable. For purchase of the lightceutical clinical code, the smart communication device 200 is connected (linked) to the financial payment server 400, and the user makes a payment by paying a fixed charge (S182). When the payment is completed via the financial payment server 400, payment completion information is sent to the information providing server 500 (S183), the information providing server 500 sends the payment information to the information providing server DB 600 (S184), and stores the payment information as additional customer-related information in the information providing server DB 600 (S185). The information providing server 500 reads the lightceutical clinical code from the information providing server DB 600 in accordance with the name of the disease and the number of times that the lightceutical clinical code is usable selected by the user (S186) and sends the read lightceutical clinical code to the smart communication device 200 (S187). In some cases, in Step S187, the information providing server 500 may send the number of times the lightceutical clinical code is usable (the remaining number of times of use) as well as the lightceutical clinical code to the smart communication device 200.

In the present disclosure, the payment used in the purchasing of the lightceutical clinical code is made in conjunction with a financial payment server or a mobile payment service generally managed by a financial institution.

The selecting of the first disease or symptom and the purchasing of the first lightceutical clinical code are for those who purchase a lightceutical clinical code for the first time.

After the purchasing of the first lightceutical clinical code, in selecting of a second disease or symptom, the disease selection screen 721 or the symptom selection screen 731, which is the UI screen through which a disease or symptom is selected via the smart communication device 200, is displayed again on the smart communication device 200, the user selects a disease or symptom to be treated, and whether a lightceutical clinical code of the selected disease or symptom has been already purchased and the number of times that the lightceutical clinical code is usable has been exhausted are determined.

After it is determined that the lightceutical clinical code of the disease or symptom selected in the selecting of the second disease or symptom has been already purchased and the number of times that the lightceutical clinical code is usable has not been exhausted, as storing a response to a self-diagnosis questionnaire, the storing of the response to the self-diagnosis questionnaire of the therapy performing flowchart of FIG. 6 in which the user inputs a current state of his or her disease or symptom is performed. That is, in the storing of the response to the self-diagnosis questionnaire, after the user checks information required for low level light therapy (i.e., therapy method information) in accordance with the self-diagnosis questionnaire displayed on the smart communication device 200, the user performs self-diagnosis in which the user inputs a current state of his or her disease or symptom (S210), and when the self-diagnosis is completed, information input to the smart communication device 200, i.e., the response to the self-diagnosis questionnaire, is encoded and sent to the information providing server 500 via the wired and wireless information networks 300 (S220), the information providing server 500 sends the information to the information providing server DB 600 (S230), and the sent self-diagnosis information is stored as additional customer-related information in the information providing server DB 600 (S240). After the storing of the response to the self-diagnosis questionnaire is completed, the process proceeds to the operating of the light therapy device (S250, S260).

After it is determined that the number of times that the lightceutical clinical code of the disease or symptom selected by the user in the selecting of the second disease or symptom is usable has been exhausted, in purchasing a second lightceutical clinical code, the user is informed of the fact that he or she needs to re-purchase the lightceutical clinical code using letters (S188), the smart communication device 200 displays a screen for purchasing the lightceutical clinical code (S181), and the smart communication device 200 is connected (linked) to the financial payment server 400 to allow the user to make a payment by paying a fixed charge (S182). When the payment is completed via the financial payment server 400, payment completion information is sent to the information providing server 500 (S183), the information providing server 500 sends the payment information to the information providing server DB 600 (S184), and stores the payment information as additional customer-related information in the information providing server DB 600 (S185). The information providing server 500 reads the lightceutical clinical code from the information providing server DB 600 in accordance with the name of the disease and the number of times that the lightceutical clinical code is usable selected by the user (S186) and sends the read lightceutical clinical code to the smart communication device 200 (S187).

The selecting of the second disease or symptom and the purchasing of the second lightceutical clinical code indicate a case in which, although a lightceutical clinical code has been already purchased, another lightceutical clinical code has to be purchased to treat a different symptom or disease.

After the purchasing of the second lightceutical clinical code is completed, in selecting a third disease or symptom, the disease selection screen 721 or the symptom selection screen 731, which is the UI screen through which a disease or symptom is selected via the smart communication device 200, is displayed again on the smart communication device 200, the user selects a disease or symptom to be treated, and whether a lightceutical clinical code of the selected disease or symptom has been already purchased and the number of times that the lightceutical clinical code is usable has been exhausted are determined. When a disease that is treated with the lightceutical clinical code re-purchased in the purchasing of the second lightceutical clinical code is selected in the selecting of the third disease or symptom, the process proceeds to the operating of the light therapy device (S250, S260).

After it is determined that the number of times that the lightceutical clinical code of the disease or symptom selected by the user in the selecting of the third disease or symptom is usable has been exhausted, in purchasing a third lightceutical clinical code, the user is informed of the fact that he or she needs to re-purchase the lightceutical clinical code using letters (S189), the smart communication device 200 displays a screen for purchasing the lightceutical clinical code (S181), and the smart communication device 200 is connected (linked) to the financial payment server 400 to allow the user to make a payment by paying a fixed service charge (S182). When the payment is completed via the financial payment server 400, payment completion information is sent to the information providing server 500 (S183), the information providing server 500 sends the payment information to the information providing server DB 600 (S184), and stores the payment information as additional customer-related information in the information providing server DB 600 (S185). The information providing server 500 reads the lightceutical clinical code from the information providing server DB 600 in accordance with the name of the disease and the number of times that the lightceutical clinical code is usable selected by the user (S186) and sends the read lightceutical clinical code to the smart communication device 200 (S187). When the purchase is completed in the purchasing of the third lightceutical clinical code, the process proceeds to the operating of the light therapy device (S250, S260).

The selecting of the third disease or symptom and the purchasing of the third lightceutical clinical code indicates a process in which, although a lightceutical clinical code of a symptom or disease to be treated has been already purchased, the number of times that the lightceutical clinical code is usable has been already exhausted, and the number of times that the lightceutical clinical code is usable has to be re-purchased.

In operating of a light therapy device, a therapy screen (i.e., a therapy performing screen) is displayed on the smart communication device 200 (S250), and the user performs light therapy using the therapy screen. Here, the lightceutical clinical code is automatically sent from the smart communication device 200 to the light therapy device 100 and the light therapy device 100 is operated in accordance with the lightceutical clinical code, or a light therapy device control signal is generated in accordance with the lightceutical clinical code sent from the smart communication device 200, the generated light therapy device control signal is sent to the light therapy device 100, and the light therapy device 100 is operated in accordance with the light therapy device control signal such that the therapy is performed by light for therapy being irradiated from the light therapy device 100 (S260).

After a light irradiation stop button is forcibly selected or a set therapy time ends during therapy in the operating of the light therapy device, in ending an operation of the light therapy device, the light therapy is automatically ended, the fact that the light therapy is ended is sent to the smart communication device 200, and after the therapy is ended, the lightceutical clinical code stored in the low level light therapy device 100 or the smart communication device 200 is cleared (initialized), and the number of times that the purchased lightceutical clinical code is usable stored in the smart communication device 200 is also updated by a predetermined number of times of therapy performed using the lightceutical clinical code (for example, four) being subtracted therefrom such that a value resulting from subtracting the number of times of therapy performed using the lightceutical clinical code (for example, four) from the number of times that the purchased lightceutical clinical code is usable is displayed on the therapy screen (S270).

After the low level light therapy using the light therapy device 100 is ended in the ending of the operation of the light therapy device, in storing therapy end information, therapy end information, i.e., an actual number of times of therapy (or therapy time interval information) and the remaining number of times that the lightceutical clinical code is usable, in addition to a therapy end notification signal, which is a signal notifying of the end of the therapy, is sent from the smart communication device 200 to the information providing server 500 (S280), the information providing server 500 sends the received signal and information to the information providing server DB 600 (S290), and the sent therapy end information is stored as additional customer information in the information providing server DB 600 (S300).

After the information providing server 500 receives the therapy end notification signal in the storing of the therapy end information, in storing a response to a therapy result questionnaire, the information providing server 500 reads a therapy result questionnaire from the information providing server DB 600 (S310) and sends the read therapy result questionnaire to the smart communication device 200 (S320). When the user selects a therapy result button and a result input button via the smart communication device 200 after therapy, the smart communication device 200 displays the therapy result questionnaire, and when the user inputs a response to the therapy result questionnaire (S330), the smart communication device 200 sends the response to the therapy result questionnaire to the information providing server 500 (S340), the information providing server 500 sends the received response to the therapy result questionnaire to the information providing server DB 600 (S350), and the received response to the therapy result questionnaire is stored as additional customer information in the information providing server DB 600 (S360).

After storage of the response to the therapy result questionnaire is completed in the storing of the response to the therapy result questionnaire, and the user selects the therapy result checking button to check his or her states before and after therapy, in outputting a therapy result, the smart communication device 200 displays the therapy result checking screen, and when the user selects a predetermined period (e.g., a week, a month, a year) button indicating a period of which the user wants to check the result via the therapy result checking screen, the smart communication device 200 sends a therapy result checking request signal for a predetermined period to the information providing server 500 (S370), the information providing server 500 sends the received signal to the information providing server DB 600 (S380), the information providing server 500 receives a therapy result of the predetermined period (that is, states of the user before and after therapy) from the information providing server DB 600 (S390) and sends the received therapy result to the smart communication device 200 (S400), and the smart communication device 200 displays the therapy result of the predetermined period by showing the therapy result related to the disease or symptom in graphs or numerical values on a weekly basis, a monthly basis, and a yearly basis to allow the user to check the therapy effect (S410).

The system and method for providing a smart communication device-based low level light therapy service of the present disclosure will be described in more detail using the embodiments below.

FIGS. 9 to 18 are views for describing an embodiment in which menstrual pain is treated using the system and method for providing a smart communication device-based light therapy service according to the present disclosure and illustrate various screens displayed on the smart communication device 200.

Figure 9:
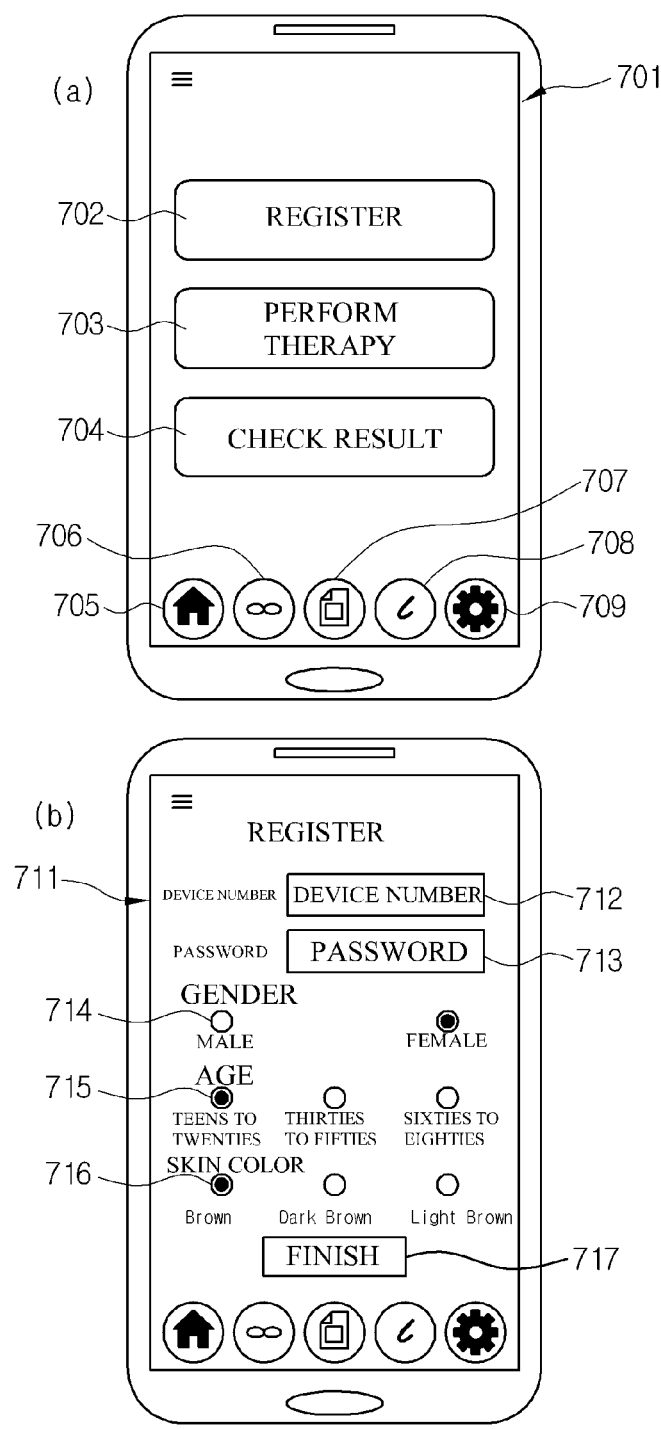
FIG. 9 illustrates examples of an initial screen and a registration screen of the light therapy application of the present disclosure.

FIG. 9 illustrates an initial screen and a registration screen of the light therapy application of the present disclosure.

FIG. 9(a) illustrates the initial screen 701 of the smart communication device-based light therapy application of the present disclosure. The initial screen 701 includes the registration button 702, a therapy button 703, and a result checking button 704. In this way, the user may input a device number and a password and log in or select the therapy button or the registration button.

The registration button 702 is a button for allowing a new user to register his or her device and register user information. The therapy button 703 is a button to be selected by the registered user to receive light therapy. The result checking button 704 is a button selected by the registered user to check the user's states before and after therapy and a therapy effect. That is, the new user selects the registration button 702 to register his or her device and register user information. The registered user may immediately perform therapy by selecting the therapy button 703 or may select the result checking button 704 when the user wants to check his or her states before and after treatment.

Quick buttons 705 to 709 may be located at the bottom of the screens of the light therapy application. The quick buttons 705 to 709 include a home quick button 705, a connection quick button 706 to perform connection to (pairing with) a light therapy device, a result checking button 707, an information quick button 708 with which therapy methods and precautions can be checked, and a settings quick button 709 for setting the light therapy application. The quick buttons 705 to 709 may also be present at the bottom of the initial screen 701 and a registration screen 711 of the light therapy application.

FIG. 9(b) illustrates the registration screen 711 of the smart communication device-based light therapy application of the present disclosure.

When the registration button 702 is selected from the initial screen 701 of the light therapy application, a device number and a password of the user's light therapy device are input to a device number input window 712 and a password input window 713, respectively, a gender radio button 714 corresponding to the user's gender is selected in a gender item, an age radio button 715 corresponding to the user's age is selected in an age item, and a skin color radio button 716 corresponding to the user's skin color is selected in a skin color item, and then a finish button 717 is selected to perform registration. For example, FIG. 9(b) illustrates a case in which a female radio button 714 is selected in the gender item, a teens-to-twenties radio button 715 is selected in the age item, and a Brown radio button 716 is selected in the skin color item. That is, FIG. 9(b) illustrates a case in which the gender is set as "female," the age is set as "teens to twenties," and the skin color is set as "Brown."

Figure 10:
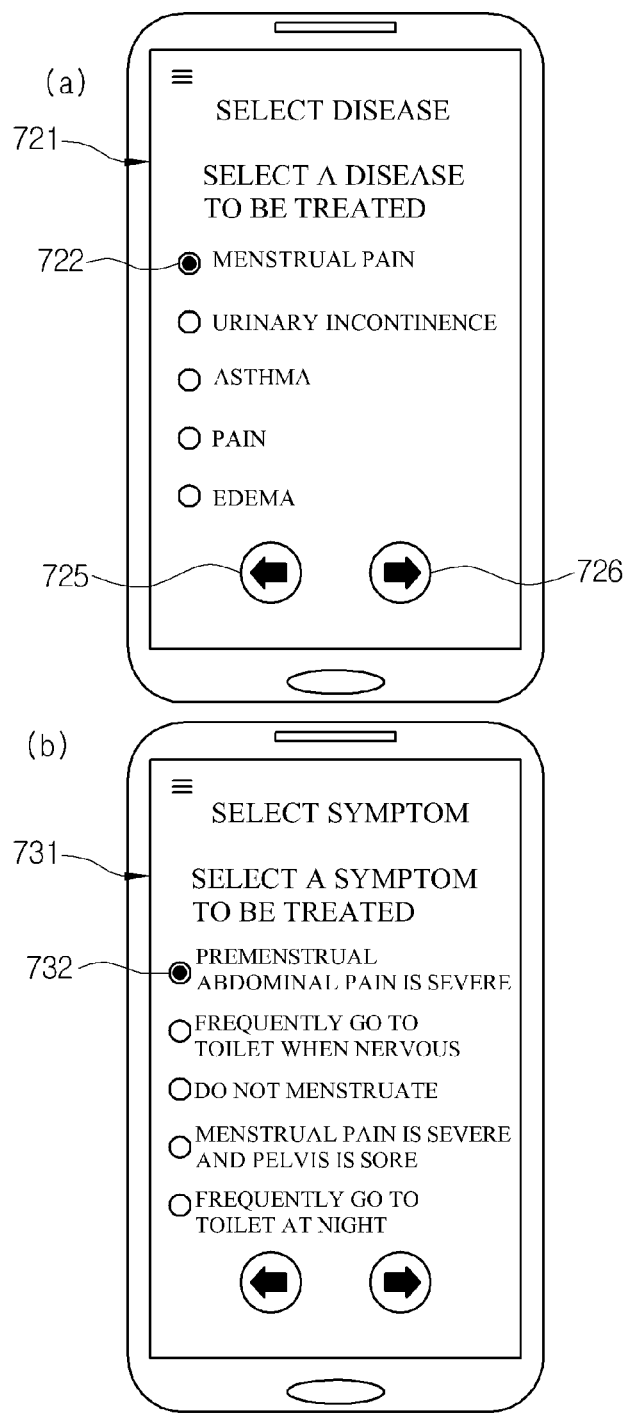
FIG. 10 illustrates examples of a disease selection screen and a symptom selection screen of the light therapy application of the present disclosure.

FIG. 10 illustrates a disease selection screen and a symptom selection screen of the light therapy application of the present disclosure.

FIG. 10(a) illustrates the disease selection screen 721 of the smart communication device-based light therapy application of the present disclosure. That is, when the therapy button 703 is selected from the initial screen 701 of the light therapy application of FIG. 9(a), the disease selection screen 721 is displayed on the smart communication device 200, various disease radio buttons 722 are presented in the disease selection screen 721, and the user selects one of the disease radio buttons 722. FIG. 10(a) illustrates a case in which a menstrual pain radio button is selected. Here, among the various disease radio buttons 722, names of diseases related to which lightceutical clinical codes are purchased may be shown differently from names of diseases related to which lightceutical clinical codes are not purchased. That is, a font color, a font shade, or a font size may differ between the names of diseases related to which lightceutical clinical codes are purchased and the names of diseases related to which lightceutical clinical codes are not purchased.

A reverse arrow button 725 and a forward arrow button 726 may be include at the bottom of the screens of the light therapy application so that the user selects the reverse arrow button 725 when the user aims to return to a previous screen and selects the forward arrow button 726 when the user aims to proceed to a subsequent process. The reverse arrow button 725 and the forward arrow button 726 are included also at the bottom of the disease selection screen 721 and the symptom selection screen 731.

The disease radio button 722 and a symptom radio button 732 selected in the disease selection screen 721 and the symptom selection screen 731 are shown with thick font (bold font), and the disease radio buttons 722 and the symptom radio buttons 732 that are not selected are shown with light grey font.

FIG. 10(b) illustrates the symptom selection screen 731 of the smart communication device-based light therapy application of the present disclosure. That is, when the therapy button 703 is selected from the initial screen 701 of the light therapy application of FIG. 9(a), the symptom selection screen 731 is displayed on the smart communication device 200, various symptom radio buttons 732 are presented on the symptom selection screen 731, and the user selects one of the various symptom radio buttons 732. In some cases, the disease selection screen 721 and the symptom selection screen 731 may be sequentially displayed. FIG. 10(b) illustrates a case in which a symptom button "Premenstrual abdominal pain is severe" is selected.

Figure 11:
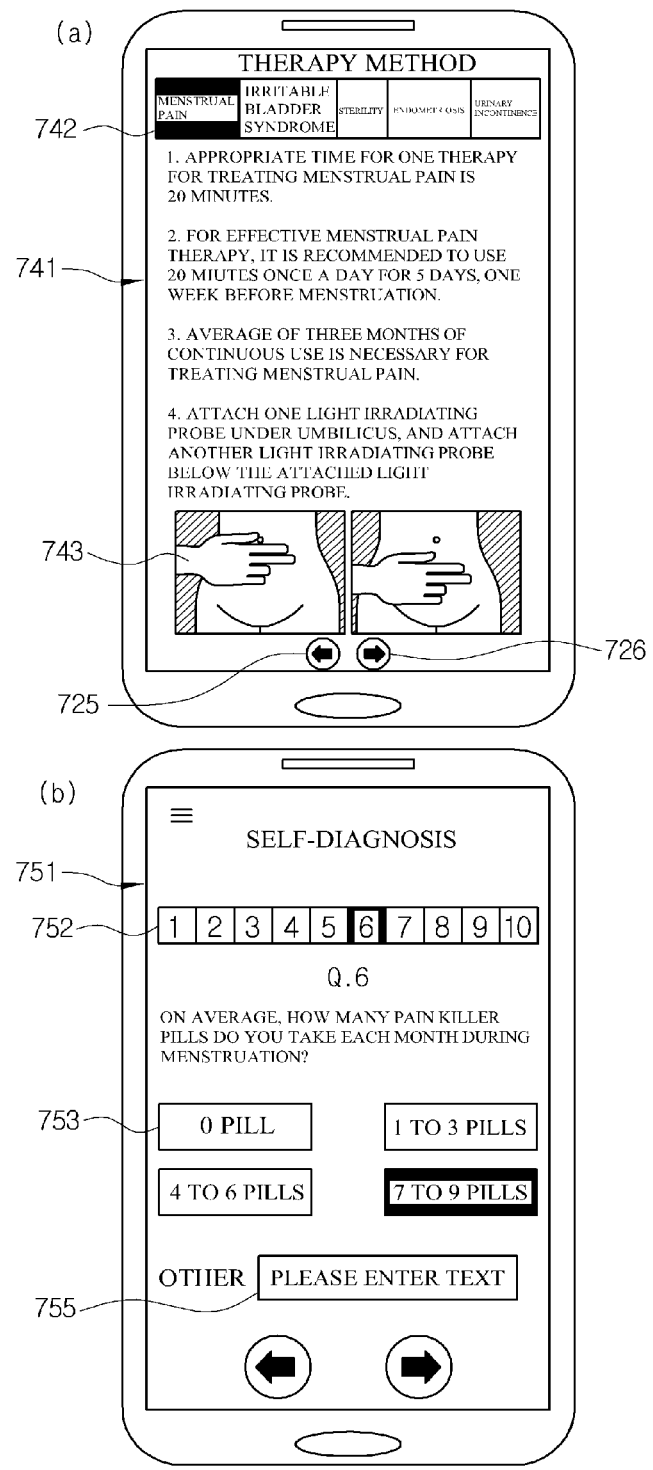
FIG. 11 illustrates examples of a therapy method screen and a self-diagnosis screen of the smart communication device-based light therapy application of the present disclosure.

FIG. 11 illustrates a therapy method guide screen and a self-diagnosis screen of the light therapy application of the present disclosure.

FIG. 11(a) illustrates a therapy method guide screen 741 of the smart communication device-based light therapy application of the present disclosure. That is, the therapy method guide screen 741 is a screen for describing a method of treating a disease selected by the user using the light therapy device 100 and is a therapy method viewing screen that provides a method of using the light therapy device 100 and precautions.

The therapy method guide screen 741 includes therapy method viewing buttons 742 for various diseases. The therapy method viewing buttons 742 for various diseases present several names of diseases for which light therapy using the light therapy device 100 can be performed, and the user selects a predetermined name of disease to view a therapy method thereof. In some cases, the therapy method viewing buttons 742 for various diseases may present several names of diseases, names of diseases related to lightceutical clinical code already purchased by the user may have a background color (or shade), and the user may view only the therapy method of the disease related to the lightceutical clinical code that he or she has already purchased.

That is, the therapy method guide screen 741 may present several names of diseases for which light therapy using the light therapy device 100 can be performed, and the user may select the therapy method viewing buttons 742 for various diseases to check therapy methods for various diseases to be treated and precautions. Information on an attachment position of a low level light therapy device for therapy in accordance with a disease, a light irradiation time per each time, a number of times that light irradiation is performed per day, an average therapy period for treating a selected disease, and precautions for attachment may be presented via the therapy method guide screen 741 using images or moving pictures 743.

FIG. 11(a) illustrates a case in which menstrual pain, irritable bladder syndrome, sterility, endometriosis, and urinary incontinence are presented in therapy method viewing buttons 742, and, among the above, menstrual pain, which is selected by the user is selected and shaded. The other diseases cannot be selected because lightceutical clinical codes related thereto have not been purchased and may be selected when the lightceutical clinical codes related thereto are purchased. The user may check information on an attachment position of a light therapy device, a method of using the light therapy device, and precautions related to a selected disease.

FIG. 11(b) illustrates a self-diagnosis screen 751 of the smart communication device-based light therapy application of the present disclosure.

The self-diagnosis screen 751 is a screen through which the user inputs a state of his or her disease in accordance with a self-diagnosis questionnaire (that is, a response to the self-diagnosis questionnaire) via the smart communication device 200 before therapy to check whether his or her diseases is well-treated. Here, the self-diagnosis questionnaire consists of standardized questions related to the user's disease in accordance with the International Classification of Diseases code. In the self-diagnosis screen 751, contents of the self-diagnosis questionnaire vary in accordance with a disease, a self-diagnosis question number indicating part 752 configured to indicate numbers of the self-diagnosis questions is present at the top, and a drug dose related to a selected disease is included in the self-diagnosis questionnaire. The user may press a predetermined number button in the self-diagnosis question number indicating part 752 and answer a predetermined self-diagnosis question.

FIG. 11(*b*) illustrates a state in which number buttons marked from 1 to 10 are included in the self-diagnosis question number indicating part 752, the number buttons represent a total number of questions, and a number button "6" is selected. Consequently, "On average, how many pain killer pills do you take each month during menstruation?" which is a sixth question (Q.6) is displayed, and four possible answers to the self-diagnosis question are presented with four possible answer buttons 753. That is, FIG. 11(*b*) illustrates a case in which the user has selected a "seven to nine pills" button as a response to the sixth question (Q.6), "On average, how many pain killer pills do you take each month during menstruation?". When possible answers are not given, the user may input content related to a state of his or her disease in a blank 755 using letters or numbers. The input self-diagnosis replies are sent to the information providing server 500 via the wired and wireless information networks and are sent to and stored in the information providing server DB 600.

Figure 12:
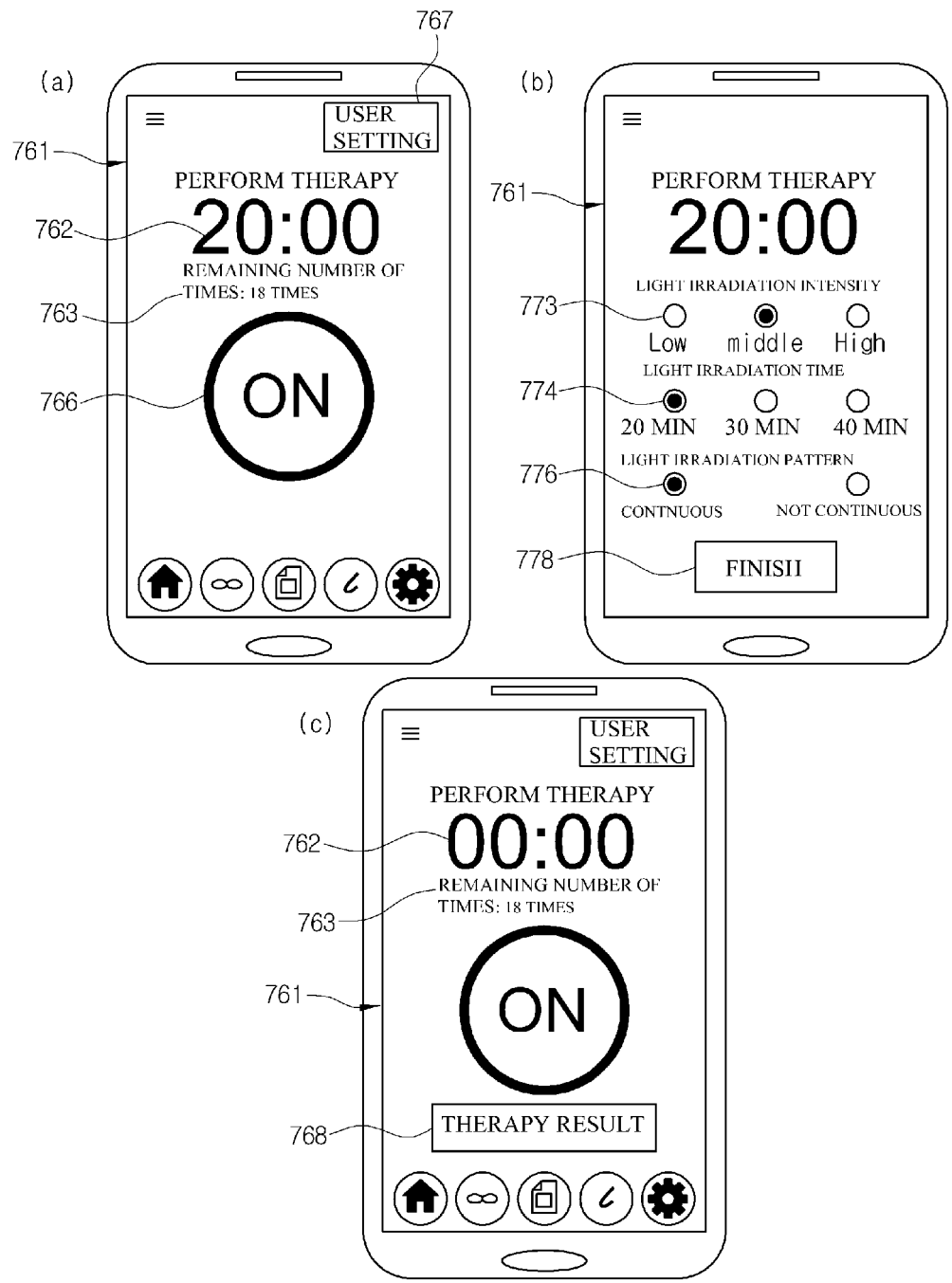
FIG. 12 illustrates examples of a therapy screen of the smart communication device-based light therapy application of the present disclosure.

FIG. 12 illustrates a therapy screen 761 of the smart communication device-based light therapy application of the present disclosure.

FIG. 12(*a*) illustrates a therapy screen before therapy begins. The therapy screen may be a screen that is displayed after the therapy button is pressed in the initial screen 701 and a disease name and a symptom are sequentially selected via the disease selection screen 721 and the symptom selection screen 731. The therapy screen 761 of FIG. 12(*a*) includes a therapy time indicating part 762, a remaining number of times of use indicating part 763, a therapy button 766, a user settings button 767, and the quick buttons 705 to 709.

The therapy button 766 is a toggle switch and is a switch for selecting a start and an end of therapy. Therapy begins when the therapy button 766 marked with "ON" is selected. Here, the therapy button 766 marked with "ON" is changed to "OFF." When the user wants to stop therapy during the therapy, the user may select the therapy button 766 marked with "OFF" to end the light therapy.

The therapy time indicating part 762 displays a remaining therapy time during the therapy.

The remaining number of times of use indicating part 763 indicates a remaining number of times that a lightceutical clinical code already purchased by the user is usable. The user may recognize the remaining number of times of use through the remaining number of times of use indicating part 763.

FIG. 12(*a*) illustrates a case in which 20 minutes remain and the remaining number of times of use is 18 times because the light therapy is not started. When the user wants to change the lightceutical clinical code in the light therapy device controller, the user may select the user settings button 767 at the top of the screen to change the lightceutical clinical code.

FIG. 12(*b*) illustrates a therapy screen 761 displayed when the user selects the user settings button 767 in the therapy screen. The user may change an intensity of light, an irradiation time of light, and an irradiation pattern of light, which are lightceutical clinical codes, by selecting suitable values using a light irradiation intensity button 773, a light irradiation time button 774, and a light irradiation pattern button 776, respectively, as needed. When a settings finish button 778 is selected, changes are saved, and a previous screen, i.e., the therapy screen just before pressing the user settings button 767, is shown.

FIG. 12(*c*) illustrates the therapy screen 761 when the light therapy is ended.

During the light therapy, the therapy button 766 in the therapy screen 761 is marked with "OFF," and when the therapy button 766 marked with "OFF" is selected or a set therapy time is elapsed, a set lightceutical clinical code is initialized, and the number of times of use already purchased by the user is deducted.

FIG. 12(*c*) illustrates a case in which the entire therapy time is elapsed, the number in the therapy time indicating part 762 becomes "00:00," and the number in the a remaining number of times of use indicating part 763 becomes 17, showing that the remaining number of times of therapy is 17 times. A therapy result button 768 is selected after an end of the treatment.

Figure 13:
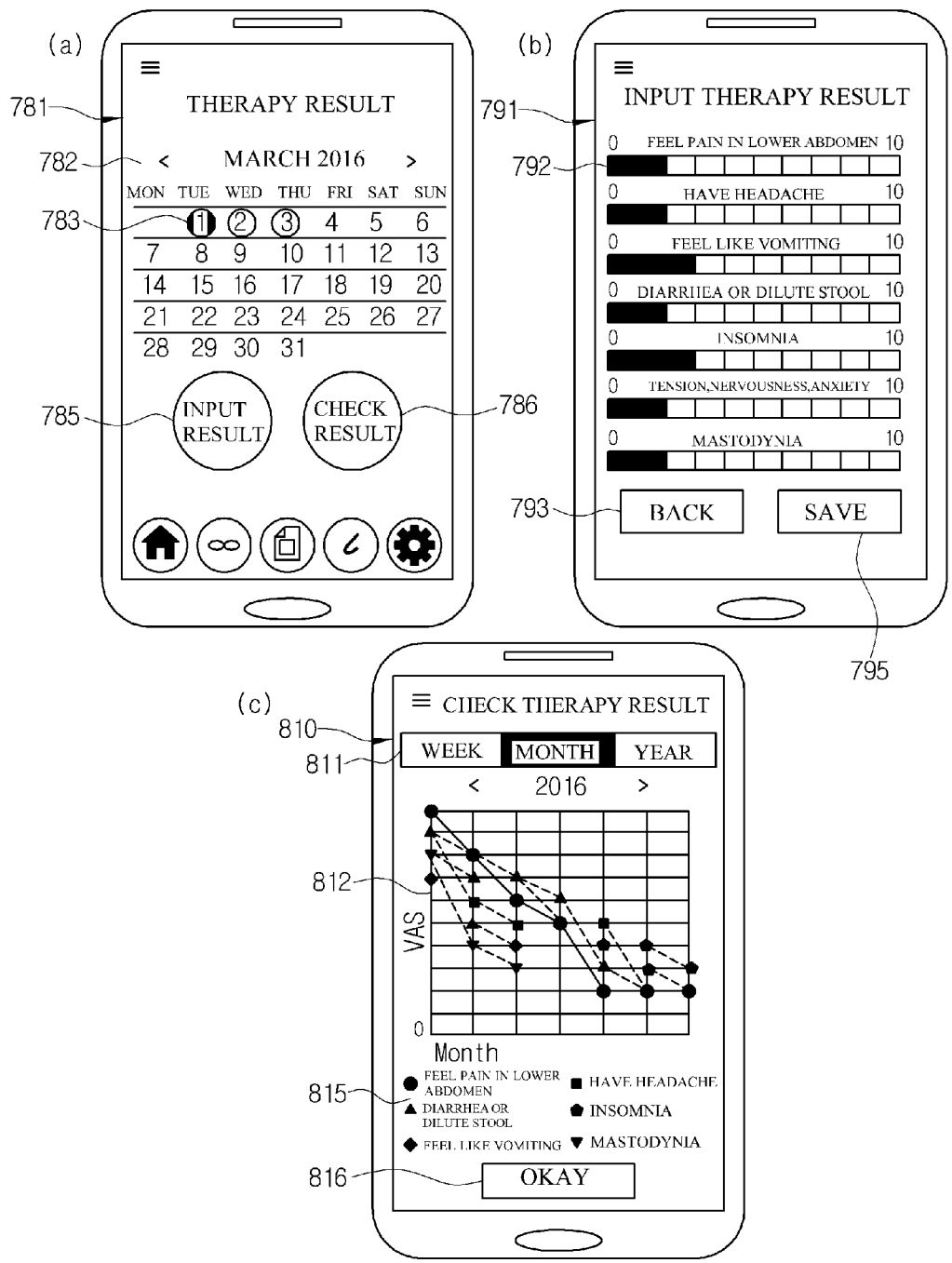
FIG. 13 illustrates examples of a therapy result input screen and a therapy result checking screen of the light therapy application of the present disclosure.

FIG. 13 illustrates examples of a therapy result input screen and a therapy result checking screen of the light therapy application of the present disclosure.

FIG. 13(*a*) illustrates a therapy result main screen 781 in the light therapy application of the present disclosure. The therapy result main screen 781 is a screen displayed when the light therapy is ended and the therapy result button 768 is selected in the therapy screen 761.

The therapy result main screen 781 includes a user calendar 782, a result input button 785, and a result checking button 786.

The user calendar 782 is displayed in the therapy result main screen 781 such that today's date, a date on which therapy is not performed among dates earlier than today, and a date on which therapy is performed among dates earlier than today are marked to be differentiated from each other. For example, in the user calendar 782, today's date is marked with a solid-line circle, a date on which therapy is not performed among dates earlier than today is marked with a dotted-line circle, and a date on which therapy is performed among dates earlier than today is marked with a solid-line circle having color.

FIG. 13(*a*) illustrates a case in which Mar. 1, 2016 is a day on which therapy is performed and is marked with a colored circle, March 2 is marked with a dotted-line circle because therapy is not performed that day, and March 3, which is today's date, is marked with a solid-line circle.

The result input button 785 is a button selected by the user when the user wants to input today's therapy result.

The result checking button 786 is a button selected by the user when the user wants to check a therapy result history.

FIG. 13(*b*) illustrates a therapy result input screen 791 displayed when the result input button 785 is selected in the therapy result main screen 781.

The therapy result input screen 791 is configured so that a therapy result is input using a therapy result input tool 792 represented with one or more of graphs, letters, and numbers.

FIG. 13(*b*) illustrates a case in which the user inputs a therapy result by selecting an extent of a therapy result state using a horizontal bar graph. When a save button 795 is pressed, the input result is sent to the information providing server 500 via the wired and wireless information networks and sent and stored in a information providing server DB 700. When the user wants to return to a previous step, the user may select a back button 793.

FIG. 13(c) illustrates a therapy result screen 810 of the light therapy application of the present disclosure.

The therapy result screen 810 is a screen displayed when input of the therapy result is completed, the result checking button 704 is selected from the initial screen 701, or the result checking button 786 is selected from the therapy result main screen 781. The therapy result screen 810 includes a period setting button 811, a graph 812, and an okay button 816.

Using period setting buttons 811 of the therapy result screen 810, by selecting one of a week, month, and year, a therapy result may be checked in a weekly basis, a monthly basis, or a yearly basis.

The graph 812 shows the response to the self-diagnosis questionnaire via the self-diagnosis screen 751 or the response to the therapy result questionnaire via the therapy result screen 810 during a period input by the period setting button 811 in numerical values and statistics. Indicators 815 shown in the graph 812 are shown using one or more of letters, numbers, and symbols below the graph 812. The indicators may be formed into questions asked through the self-diagnosis questionnaire or the therapy result questionnaire.

The okay button 816 is a button selected by the user when checking a therapy result is completed.

Figure 14:
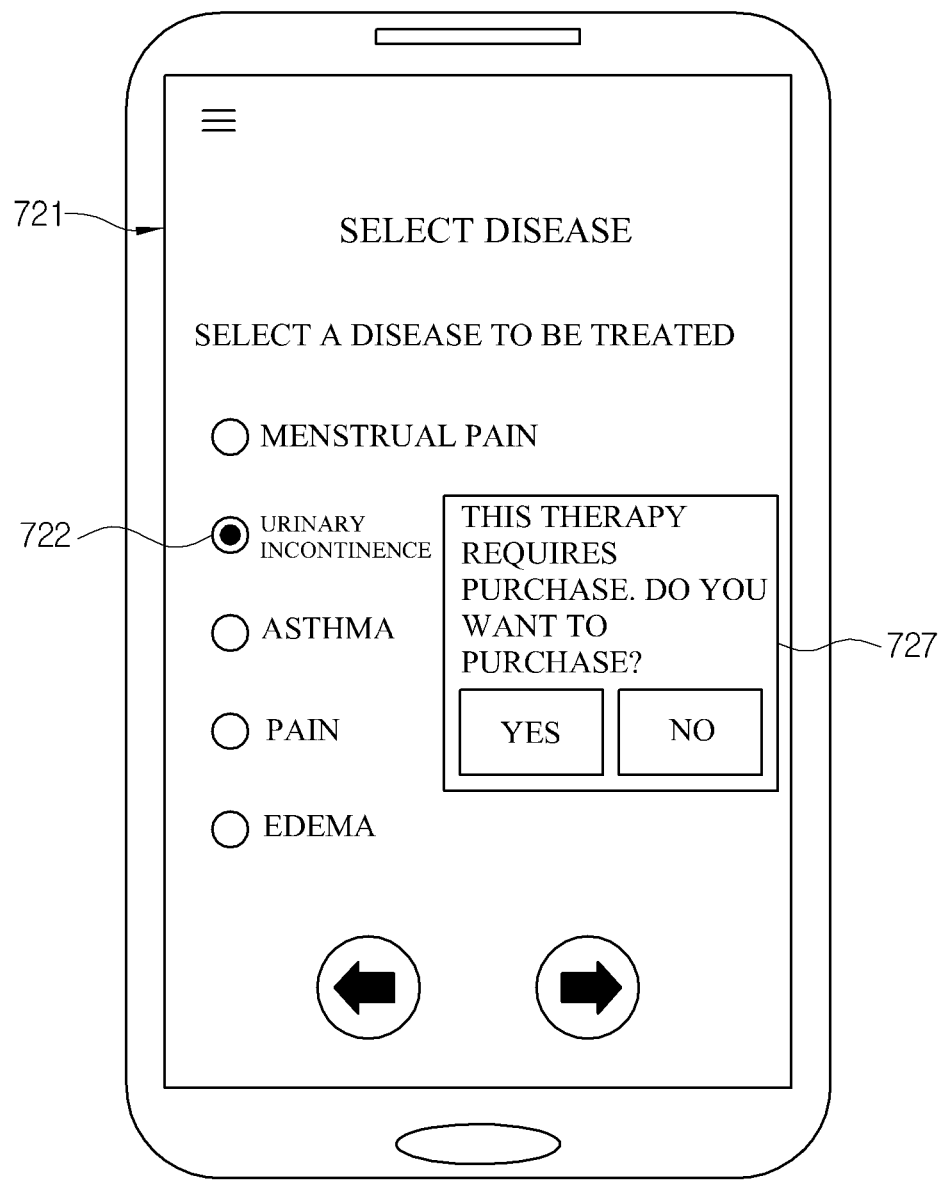
FIG. 14 illustrates an example of a disease selection screen (721) of the present disclosure in a case in which a lightceutical clinical code related to a selected disease is not purchased.

FIG. 14 illustrates an example of a case in which the user does not have a lightceutical clinical code related to a disease selected via the disease selection screen 721 of the present disclosure.

In the disease selection screen 721, a name of a disease related to which the user has purchased a lightceutical clinical code and a name of a disease related to which the user has not purchased a lightceutical clinical code may be differentiated from each other by different fonts, font colors, underlines, and the like. For example, a name of a disease related to which a lightceutical clinical code has been purchased may be shown with a bold font or black font, and a name of a disease related to which a lightceutical clinical code has not been purchased may be shown with a normal font or grey font.

When the user has not purchased and does not own (have) a lightceutical clinical code related to a disease selected by himself or herself via the disease selection screen 721, a purchase guide pop-up window 727 is displayed on the disease selection screen 721. The purchase guide pop-up window 727 informs the user that the user does not own a lightceutical clinical code related to the disease selected by himself or herself and makes the user select whether to purchase the lightceutical clinical code.

FIG. 14 illustrates a case in which the user who has already purchased a lightceutical clinical code related to menstrual pain aims to treat urinary incontinence and selects "urinary incontinence." Here, "This therapy requires purchase. Do you want to purchase?" is displayed on the purchase guide pop-up window 727, and simultaneously, the user is made to select one of a "Yes" button and a "No" button. Consequently, the user selects the "Yes" button when the user wants to make a purchase, and when the user selects the "No" button, the currently-used disease selection screen or symptom selection screen is shown again.

Figure 15:
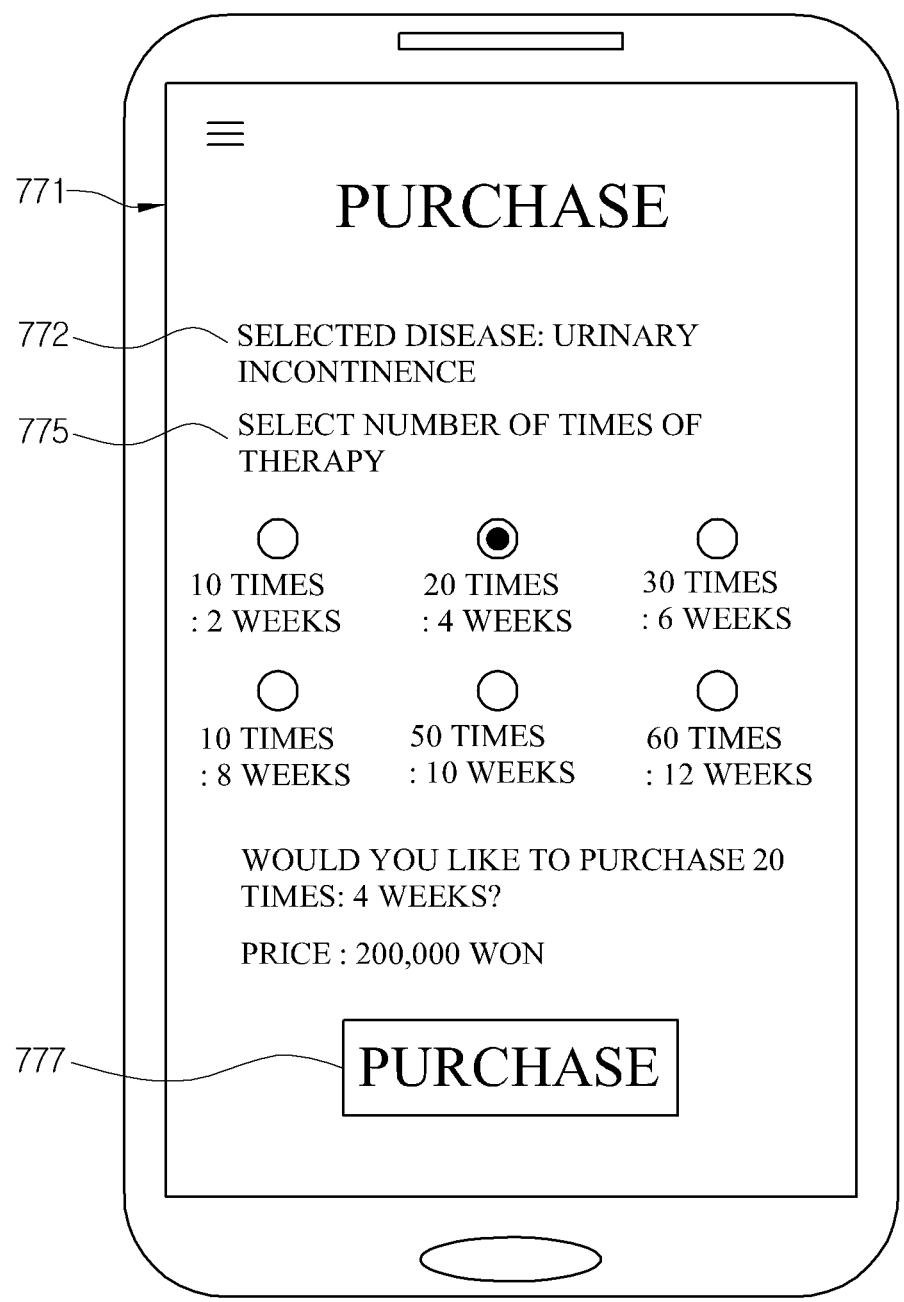
FIG. 15 illustrates an example of a purchase screen (771) presented when a lightceutical clinical code is purchased or a number of times that the lightceutical clinical code is usable is additionally purchased via the light therapy application of the present disclosure.

FIG. 15 illustrates an example of a purchase screen 771 presented when a lightceutical clinical code is purchased or a number of times that the lightceutical clinical code is usable is additionally purchased via the light therapy application of the present disclosure. Here, a name of a disease selected by the user is displayed in a disease item 772 of the purchase screen 771, a number of times of therapy to be performed using a lightceutical clinical code of the selected disease, i.e., the number of times that the lightceutical clinical code is usable, is selected in a number of times selection item 775, and a purchase button 777 is selected to make a purchase.

FIG. 15 illustrates a case in which a disease related to a lightceutical clinical code that the user wishes to purchase displayed in the disease item 772 is "urinary incontinence," and the number of times that the lightceutical clinical code is usable selected by the user in the number of times selection item 775 is "20 times: 4 weeks."

When the user wishes to additionally purchase the number of times that the lightceutical clinical code is usable, the user may select or input a name of a disease, related to the lightceutical clinical code of which the number of times of use is wished to be additionally purchased, in the disease item 772 of the purchase screen 771, and select and purchase a required number of times of use.

When a purchase list is checked and a purchase button 777 is selected on the screen, the purchase is made in conjunction with a financial payment server generally managed by a financial institution or a mobile payment service (e.g., Google Pay, Samsung Pay, Kakao Pay, Naver Pay, Payco, SSG Pay, L-Pay, Apple Pay, and Ali Pay).

Figure 16:
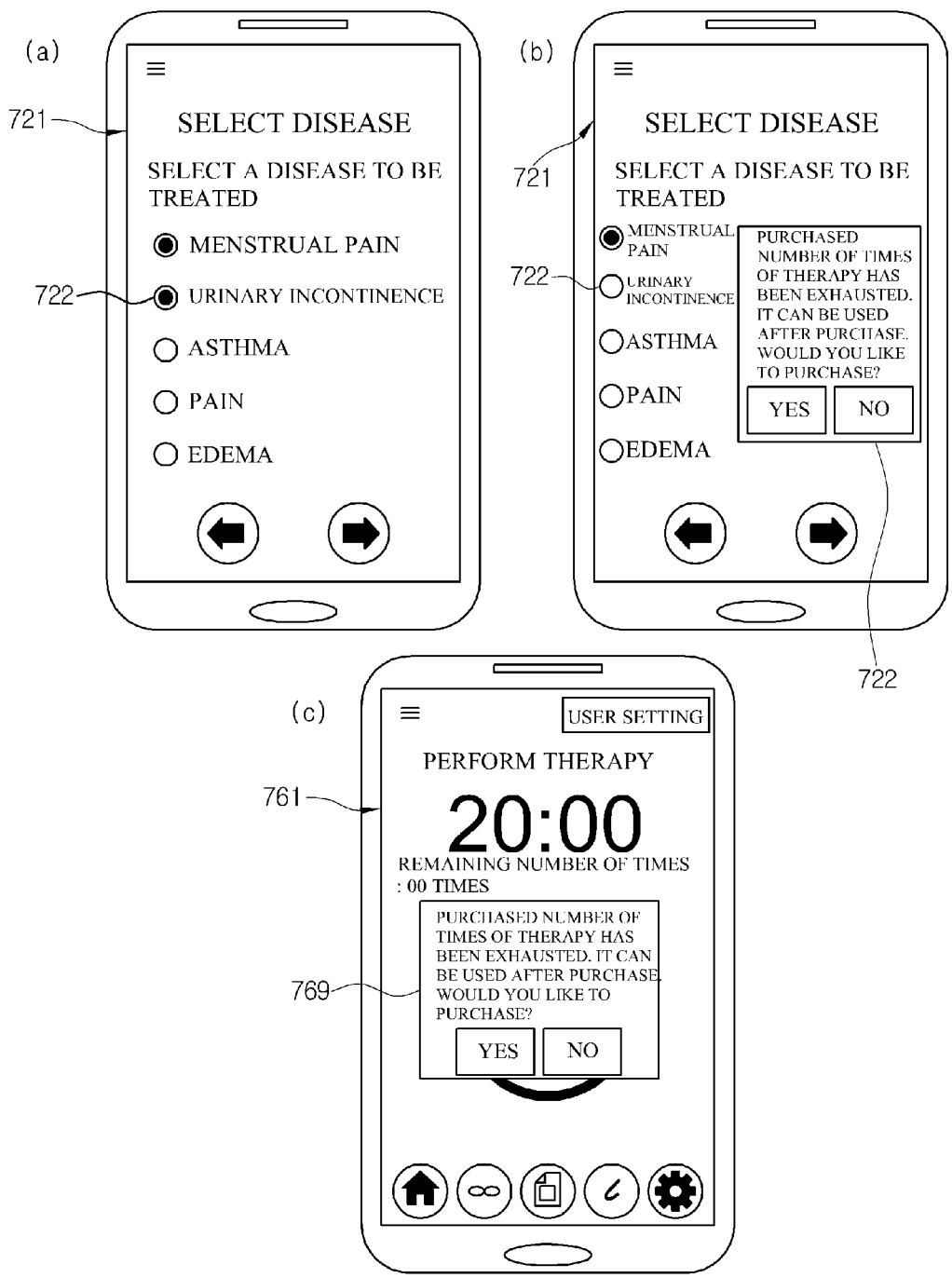
FIG. 16 illustrates an example of the disease selection screen when a lightceutical clinical code is additionally purchased via the light therapy application of the present disclosure and examples of the disease selection screen and the therapy screen when the number of times that the lightceutical clinical code is usable is exhausted.

FIG. 16 illustrates an example of the disease selection screen when a lightceutical clinical code is additionally purchased via the light therapy application of the present disclosure and examples of the disease selection screen and the therapy screen when the number of times that the lightceutical clinical code is usable is exhausted.

FIG. 16(a) illustrates an example of the disease selection screen 721 when a lightceutical clinical code of another disease is additionally purchased in the light therapy application. FIG. 16(a) illustrates a case in which the user has purchased a lightceutical clinical code for "urinary incontinence" in addition to a lightceutical clinical code for "menstrual pain." In the disease selection screen 721, the font color and font size of "menstrual pain" and "urinary continence" are different from those of "asthma," "pain," and "edema," for which lightceutical clinical codes are not purchased by the user.

FIG. 16(b) illustrates an example of the disease selection screen 721 when the number of times that the lightceutical clinical code is usable has been exhausted in the light therapy application. When the number of times that the lightceutical clinical code purchased by the user is usable is exhausted, a screen that requests for additional purchase of the number of times that the lightceutical clinical code is usable is presented as the pop-up window 727 even for the disease related to which the lightceutical clinical code and the number of times that the lightceutical clinical code is usable have been previously purchased. When the user wants to make additional purchase, the user selects a "Yes" switch (that is, a switch that indicates a decision to make purchase) in the pop-up window 727 and may purchase the number of times that the lightceutical clinical code is usable via the purchase screen 771 illustrated in FIG. 15. When the user does not want to make additional purchase, the user selects a "No" switch, and in this case, the disease selection screen or the symptom selection screen is shown again.

FIG. 16(c) illustrates an example of the therapy screen 761 when the number of times that the lightceutical clinical code is usable is exhausted while light therapy is performed via the therapy screen 761 of the light therapy application. When the user selects the therapy button 703 in the initial screen 701, the therapy screen shown in FIG. 10(a) is presented, and a value larger than "00" is displayed as the remaining number of times. However, in a case in which the number of times that the lightceutical clinical code is usable is exhausted, and "00" is displayed as the remaining number of times in the therapy screen 761, when the user selects the ON button 766 in the therapy screen, a pop-up window 769 that requests for additional purchase of the number of times that the lightceutical clinical code is usable is displayed. The additional purchase of the number of times that the lightceutical clinical code is suable is made via the purchase screen 771.

Figure 17:
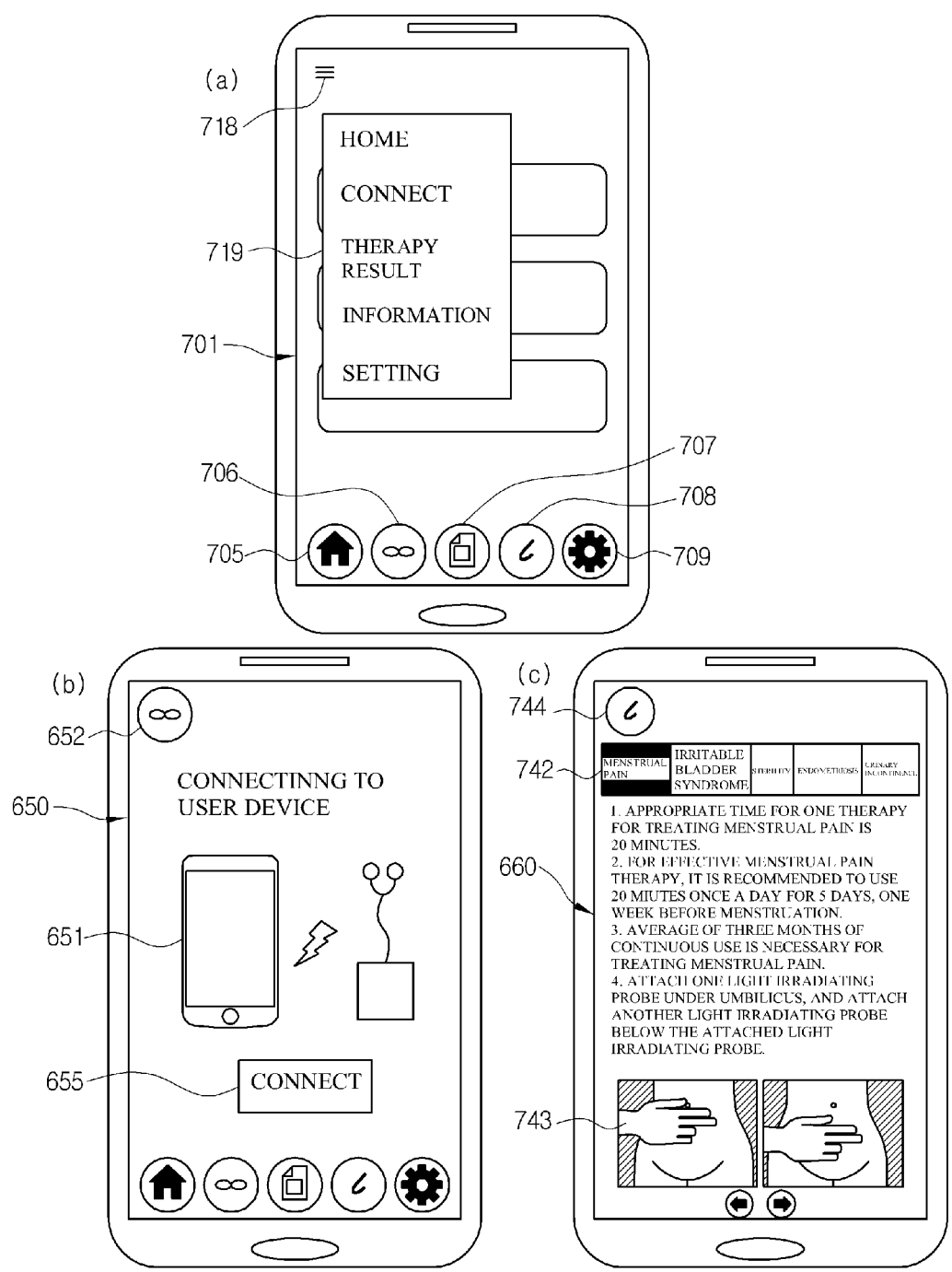
FIG. 17 illustrates examples of a quick menu pop-up window, a connect screen, and an information output screen of the light therapy application of the present disclosure.

FIG. 17 illustrates examples of a quick menu pop-up window, a connect screen, and an information output screen of the light therapy application of the present disclosure.

FIG. 17(a) illustrates an example of a quick menu pop-up window 719 in the light therapy application. That is, when the user selects a quick menu selection button 718 located at the top of the light therapy application, the quick menu pop-up window 719 for the quick buttons 705 to 709 located at the bottom of the light therapy application is displayed. FIG. 17(a) illustrates a case in which a quick menu for home, connect, therapy result, information, and settings is displayed.

FIG. 17(b) illustrates a connect screen displayed when a wireless connection using the quick menu is performed in the light therapy application. A connect screen 650 is displayed when a "connect" button is selected in the quick menu pop-up window 719 or a connect quick button 706 is selected. A connection indicator (more specifically, a wireless device connection indicator) 652 is displayed at the top of the connect screen 650 of FIG. 17(b), an image or moving picture 651 that shows connection between the smart communication device 200 and the wireless type light therapy device 100 is displayed in the middle of the screen, and when a connect button 655 is selected, the smart communication device 200 and the light therapy device 100 are connected.

FIG. 17(c) illustrates an example of an information output screen 741 in the light therapy application. Information such as a therapy method for a currently-treated disease and precautions is displayed when an "information" button is selected in the quick menu pop-up window 719 or an information quick button 708 is selected, and the user may check the information. An information provision indicator is shown on the information output screen 741, and content such as that in the therapy method guide screen 741 of FIG. 11 is displayed. The information output screen 741 allows the user to immediately view a therapy method in accordance with a disease and precautions without an inconvenience of having to check a therapy method and precautions after performing the self-diagnosis. In the information output screen 741, names of diseases that may be treated with the light therapy device are presented at the top, when a disease name is selected, the selected disease name is shaded, and a therapy method and precautions are presented using images or moving pictures. FIG. 17(c) illustrates a case in which menstrual pain, irritable bladder syndrome, sterility, endometriosis, and urinary incontinence are presented as diseases that may be treated with the light therapy device with the disease selection buttons 742, menstrual pain is selected among the diseases, and a therapy method for menstrual pain and precautions are shown. A therapy method and an attachment method are presented with the images 743 at the bottom of the information output screen 741.

Figure 18:
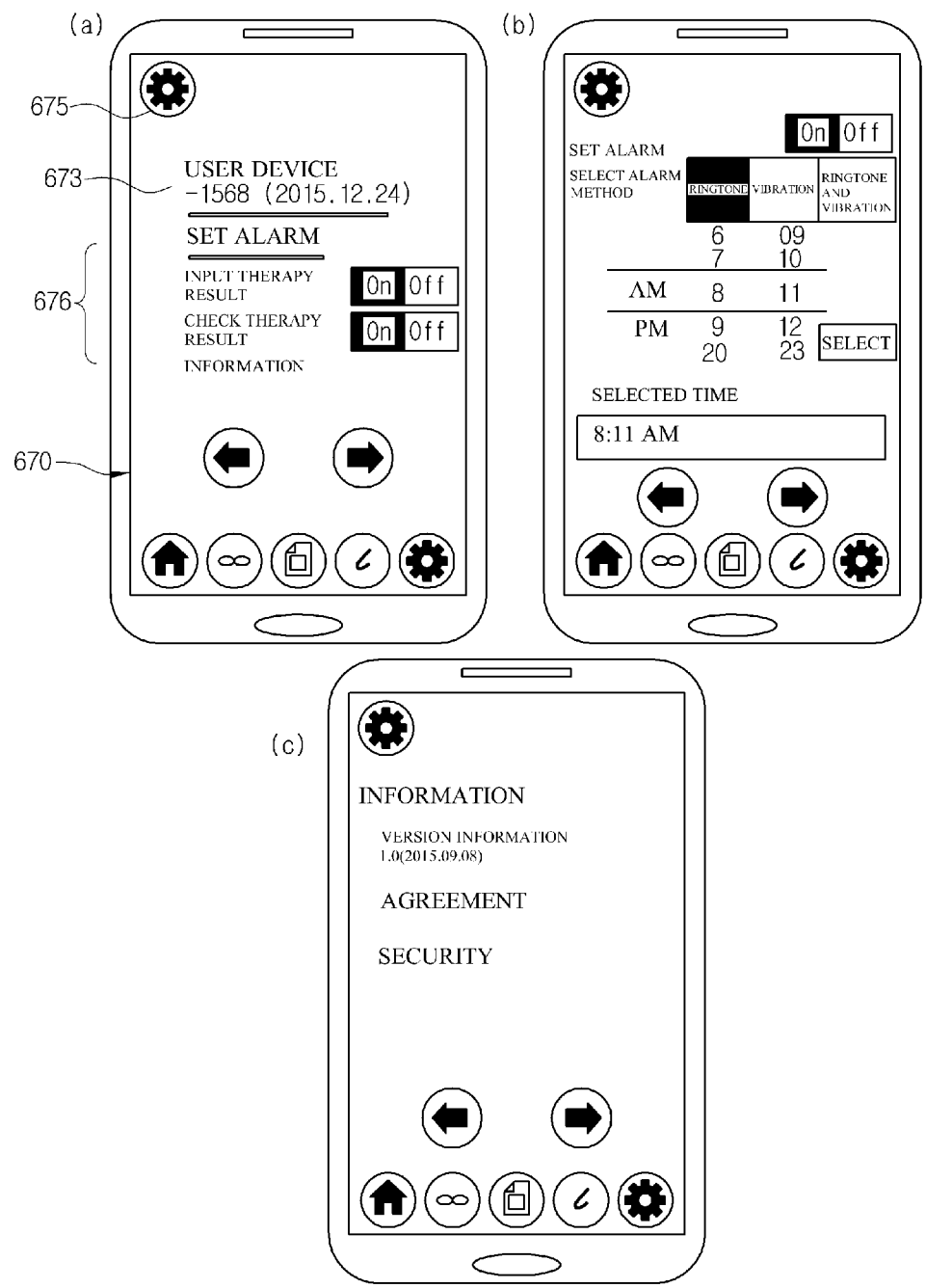
FIG. 18 illustrates examples of setting screens of the light therapy application of the present disclosure.

FIG. 18 illustrates an example of setting screens of the light therapy application of the present disclosure. A setting indicator 675 is displayed on the top of the setting screens 670, 671, and 672.

FIG. 18(a) illustrates an example of a settings main screen 670 in the light therapy application. The settings main screen 670 is output when a "setting" button is selected in the quick menu pop-up window 719 or a settings quick button 709 is selected. The settings main screen 670 outputs registration information 673 of the user's light therapy device and includes a settings unit 676. The settings unit 676 includes a set alarm selection button, a therapy result input on/off button, a therapy result checking on/off button, and an information button. The therapy result input on/off button and the therapy result checking on/off button turns an output of the therapy result input screen and an output of the therapy result checking screen on or off in accordance with a user's choice. FIG. 18(a) illustrates a case in which, referring to the registration information 673 of the light therapy device, a device number of the user's light therapy device is 15685, and a date of registration is Dec. 24, 2015, and inputting a therapy result and checking a therapy result are both turned on. The user selects the reverse arrow button 725 when the user wants to return to a previous screen, and the user selects the forward arrow button 726 when the user wants to proceed to a subsequent process. FIG. 18(b) illustrates an example of an alarm setting screen 671 of the setting screens. The alarm setting screen 671 is displayed when the set alarm selection button is selected in the settings unit 676. The alarm setting screen 671 includes an alarm setting on/off button, an alarm method selection button, an alarm time setting unit 679, an a selection button 677. The alarm setting on/off button is configured to be turned on or off in accordance with whether to set an alarm, and the alarm method selection button is configured such that one of a ringtone, vibration, both ringtone and vibration is selected as an alarm. The alarm time setting unit 679 allows the user to select a desired therapy time, i.e., and alarm time, using the selection button 677, and the alarm time selected in this way is displayed on a selected time window 681. FIG. 18(b) illustrates a case in which alarm setting is turned on, a ringtone is selected as an alarm method, and an alarm time is 8:11 am.

FIG. 18(c) illustrates an example of a system information screen 672 of the setting screens. The system information screen 672 is displayed when an information (or system information) selection button is selected in the settings unit 676 of the settings main screen 670. Information 678 on a light therapy service providing system including version information of an installed light therapy application, agreement, security, and the like is output on the system information screen 672. FIG. 18(c) illustrates a case in which version information of the light therapy application is 1.0, and an update date is Sep. 8, 2015. Content related to agreement and security is general content related to a mobile application service and may be easily understood and implemented in various ways by one of ordinary skill in the art even without description thereof. Therefore, one of ordinary skill in the art may easily understand and implement agreement and security in various ways.

Figures 19, 20:
FIG. 19 is an example of a list of information for each device number of a light therapy device for describing information stored in an information providing server database (DB) of the system for providing a light therapy service of the present disclosure.
FIG. 20 is a therapy history screen linked to the information providing server DB of the system for providing a light therapy service of the present disclosure.

FIG. 19 is an example of a list of information for each device number of a light therapy device for describing information stored in an information providing server DB of the system for providing a light therapy service of the present disclosure.

A device number (i.e., a device number of a light therapy device), a date of registration, a treated disease, gender, age, skin color, a number of times of therapy (i.e., a number of times that a lightceutical clinical code is usable upon purchasing), and a remaining number of times (i.e., a remaining number of times that the lightceutical clinical code is usable) are stored in the information providing server DB 600. The list of information for each device number of a light therapy device of FIG. 19 may be checked by a manager via a monitor of the information providing server 500 or by the user via the smart communication device 200. In some cases, the smart communication device 200 may be configured such that only personal information of the user and the number of times that a lightceutical clinical code is usable in accordance with a device number of the light therapy device owned by the user may be checked via the smart communication device 200.

FIG. 20 is a therapy history screen linked to the information providing server DB of the system for providing a light therapy service of the present disclosure. That is, FIG. 20 illustrates a therapy history screen that is presented when a predetermined device number of a light therapy device is selected from the list of information for each device number of a light therapy device of FIG. 19. A calendar 682 is presented for checking therapy history, a day 683 on which therapy is performed is marked with a circle that has a specific background color or is shaded, a day on which therapy is not performed is marked with a dotted-line circle, and today's date is marked with a solid-line circle. When the user checks a therapy history and selects an okay button 685, the screen displaying a list of information for each device number of FIG. 19 is shown again.

According to the system and method for providing a smart communication device-based light therapy service of the present disclosure, a light therapy device is operated in conjunction with a smart communication device and an information providing server to perform a light therapy, and when a user purchases a lightceutical clinical code corresponding to a certain disease using the smart communication device, the information providing server generates the lightceutical clinical code of the disease containing a wavelength of light, an intensity of light, an irradiation time of light, and an irradiation pattern of light and sends the generated lightceutical clinical code to the smart communication device, and the smart communication device sends the received lightceutical clinical code to the light therapy device or generates a light therapy device control signal in accordance with the lightceutical clinical code and transmits the generated light therapy device control signal to the light therapy device to operate the light therapy device, thereby allowing customized therapy of various diseases or symptoms of a user to be conveniently and safely performed anytime and anywhere.

Further, in the present disclosure, the smart communication device performs a function of registering a light therapy device and inputting user information via a UI screen, a function of presenting several names of diseases or symptoms and allowing a user to select a disease name or symptom to be treated, a function of providing information on a low level light therapy method related to the selected disease name or symptom to the user with letters, images, photographs, or moving pictures, a function of allowing a user to input and store a state of his or her disease or symptom before light therapy, a function of allowing the user to change the lightceutical clinical code as needed, and a function of performing low level light therapy.

Further, the smart communication device performs a function of allowing the user to input and store a state of his or her disease or symptom after the light therapy, a function of allowing the user to check the states of his or her disease or symptom before and after the light therapy in graphs or numerical values on a weekly basis, a monthly basis, and a yearly basis, a function of allowing the user to purchase a lightceutical clinical code of the disease or symptom that he or she wishes to treat using the smart communication device, and a function of allowing data input by the user to be sent to an information providing server via wired and wireless information networks and stored in a customer information DB of the information providing server.

The present disclosure connects the smart communication device and the low level light therapy device via a wire or wirelessly, thereby allowing a user to safely and conveniently perform customized therapy for his or her disease anytime and anywhere.

Currently, there are many devices that diagnose or measure diseases using smart communication devices. However, there is no system for providing a smart communication device-based low level light therapy service that allows a user to safely and conveniently treat his or her disease as in the present disclosure. That is, the present disclosure allows a user to check a state of his or her disease or symptom after therapy on a weekly, monthly, yearly basis to check a therapy effect. Also, the present disclosure is configured so that the user purchases lightceutical clinical codes corresponding to various diseases or symptoms as needed and uses the lightceutical clinical codes. In this way, the user does not have to own various light therapy devices and can perform customized light therapy by purchasing lightceutical clinical codes as needed. Further, the user can perform therapy while referring to a description of a light therapy method that is performed using a light therapy device in accordance with a disease.

Therefore, the present disclosure can newly create the smart communication device-based therapy device market.

Although not described in detail using drawings in the present specification, the system and method for providing a smart communication device-based light therapy service according to the present disclosure may be applied to treat numerous diseases that may be treated with low level light therapy by connecting a low level light therapy device to a smart communication device via a wire or wirelessly. For example, the system and method for providing a smart communication device-based light therapy service according to the present disclosure may be applied to a device for treating neck and shoulder pain, a device for treating arthritis, a device for treating Alzheimer, a device for treating stroke, a device for treating migraine, a device for treating depression, a device for treating angina, a device for treating asthma, a device for treating chronic obstructive pulmonary disease (COPD), a device for treating gastritis and gastric ulcer, a device for treating urinary continence, a device for treating prostate, a device for treating sterility, a device for treating a wrist and hand muscle symptom, a device for treating premenstrual symptom (PMS), a device for treating edema, a device for treating rhinitis, and the like.

Although specific exemplary embodiments of the present disclosure have been illustrated and described above, the present disclosure is not limited to the above-described embodiments, and one of ordinary skill in the art to which the present disclosure pertains should be able to modify and practice the present disclosure in various other ways.

INDUSTRIAL APPLICABILITY

The system and method for providing a smart communication device-based light therapy service according to the present disclosure can be applied to a device for treating neck and shoulder pain, a device for treating arthritis, a device for treating Alzheimer, a device for treating stroke, a device for treating migraine, a device for treating depression, a device for treating angina, a device for treating asthma, a device for treating chronic obstructive pulmonary disease (COPD), a device for treating gastritis and gastric ulcer, a device for treating urinary continence, a device for treating prostate, a device for treating sterility, a device for treating a wrist and hand muscle symptom, a device for treating premenstrual symptom (PMS), a device for treating edema, a device for treating rhinitis, and the like.

What is claimed is:

1. A system for providing a smart communication device-based light therapy service, the system comprising:
    a smart communication device through which a screen for purchasing a lightceutical clinical code including a wavelength of light, an intensity of light, an irradiation time of light, and an irradiation pattern of light is output and configured to receive a lightceutical clinical code from an information providing server and send the received lightceutical clinical code to a light therapy device or generate a light therapy device control signal in accordance with the lightceutical clinical code and send the generated light therapy device control signal to the light therapy device when a payment for a purchase of the lightceutical clinical code is completed in conjunction with a financial payment server;
    the information providing server configured to read the lightceutical clinical code from an information providing server database (DB) and send the read lightceutical clinical code to the smart communication device when the payment for the lightceutical clinical code is completed by the smart communication device operating in conjunction with the financial payment server; and
    the light therapy device including a light source and configured to operate in accordance with the lightceutical clinical code or the light therapy device control signal received from the smart communication device to irradiate light by a light irradiating electrode;
    wherein a number of times that the lightceutical clinical code is usable is limited, and the number of times that the lightceutical clinical code is usable is stored in the information providing server DB and reduced in accordance with a number of times that the light therapy device is operated;
    wherein the lightceutical clinical code is different in accordance with a disease or symptom;
    wherein, before an operation of the light therapy device is started, the smart communication device is configured to display a self-diagnosis screen including questionnaire items related to a drug dose of a certain disease and send a response to the self-diagnosis questionnaire input by a user via the self-diagnosis screen to the information providing server, and the information providing server is configured to store the response to the self-diagnosis questionnaire in the information providing server DB;
    wherein, when the operation of the light therapy device is ended, the smart communication device is configured to display a therapy result input screen including questionnaire items related to a degree of pain and send a response to a therapy result questionnaire input by the user via the therapy result input screen to the information providing server, and the information providing server is configured to store the response to the therapy result questionnaire in the information providing server DB;
    wherein the smart communication device is configured to display a disease selection screen through which a name of a disease to be treated is to be selected before the light therapy device is operated, display a notification that a lightceutical clinical code of a selected disease name is not purchased and a pop-up window that asks whether to purchase the lightceutical clinical code of the selected disease name when the lightceutical clinical code of the disease name selected via the disease selection screen has not already been purchased, and output a purchase screen when a switch indicating a decision to purchase the lightceutical clinical code is selected in the pop-up window;
    wherein the number of times that the lightceutical clinical code is usable is displayed on the smart communication device;
    wherein, when the number of times that the lightceutical clinical code is usable is exhausted, the smart communication device is configured to display a notification that the number of times that the lightceutical clinical code is usable has been exhausted and a pop-up window that asks whether to purchase the number of times that the lightceutical clinical code is usable and output a purchase screen when a switch indicating a decision to purchase the number of times that the lightceutical clinical code is usable is selected in the pop-up window to allow a payment for an additional purchase of the number of times that the lightceutical clinical code is usable; and
    wherein the smart communication device is configured to operate the light therapy device through a therapy screen and, upon receiving a lightceutical clinical code, configured to send a changed lightceutical clinical code to the light therapy device or generate a light therapy device control signal in accordance with the changed lightceutical clinical code and send the generated light therapy device control signal to the light therapy device.

2. The system of claim 1, wherein the light source of the light therapy device is any one of a three-color LED, an organic LED (OLED), a quantum dot LED (QLED), and an active matrix OLED (AMOLED).

3. The system of claim 1, wherein a device number of the light therapy device is registered in the information providing server via the smart communication device.

4. The system of claim 1, wherein, upon registering the light therapy device, registration information including a device number of the light therapy device, a password, a gender of the user, an age of the user, and a skin color of the user input via the smart communication device is sent to the information providing server, and the information providing server is configured to store the registration information therein.

5. The system of claim 1, wherein the smart communication device displays information related to a therapy method using the light therapy device including light irradiating electrode attachment positions in accordance with diseases using letters, images, photographs, or moving pictures.

6. The system of claim 1, wherein the smart communication device is configured to statistically process the response to the therapy result questionnaire or the response to the self-diagnosis questionnaire stored in the information providing server DB and display the responses in weeks, months, and years.

7. The system of claim 1, wherein the smart communication device is any one of a smartphone or smart watch (wrist-worn smartphone) that uses one of Android operating system (OS), Android Wear OS, Android Open Source Project OS, Apple iOS, Tizen OS, MS window OS, BlackBerry OS, FireFox OS, and MiUi Color OS as an OS.

8. The system of claim 1, wherein the light therapy device includes the light irradiating electrode and a light therapy device controller and is mounted in any one of a headgear, a patch, a necklace, a bracelet, a watch, a belt, a wrist band, a glove, a waist support, a shirt, and underpants.

9. The system of claim 1, wherein the lightceutical clinical code is in a form of a number or a combination of numbers and letters by encoding values of the wavelength of light, the intensity of light, the irradiation time of light, and the irradiation pattern of light.

10. The system of claim 1, wherein the smart communication device has a light therapy application received from the information providing server installed therein, and the light therapy application is on the basis of any one of the Android OS, the Android Wear OS, the Android Open Source Project OS, the Apple iOS, the Tizen OS, the MS window OS, the BlackBerry OS, the FireFox OS, and MiUi Color OS.

11. The system of claim 1, wherein any one of a get method and a post method is used as a method of transmitting data between the smart communication device and the information providing server to encode the data with any one of an application programming interface (API) method and a Plug-In method and send the data.

12. The system of claim 10, wherein a user interface (UI) language of the light therapy application is one of national languages.

13. The system of claim 10, wherein names of diseases are presented on a screen of the light therapy application.

14. The system of claim 5, wherein the information related to a therapy method using the light therapy device further include a light irradiation time per each time, a number of times that light irradiation is performed per day, an average therapy period for each disease, and precautions.

15. The system of claim 1, wherein the questionnaire items related to the self-diagnosis screen and the therapy result input screen comply with questionnaire items of internationally standardized questionnaires.

16. The system of claim 1, wherein:
the smart communication device and the light therapy device are connected via a wire or wirelessly;
when the smart communication device and the light therapy device are wirelessly connected, the smart communication device and the light therapy device are connected using any one of Zigbee, Bluetooth, near-field communication (NFC), wireless fidelity (Wi-Fi), and radio frequency (RF);
when the smart communication device and the light therapy device are connected via a wire, the smart communication device and the light therapy device are connected using a USB terminal, an iPhone terminal, Recommended Standard-232C (RS232C), Inter-integrated circuit (I2C), or serial peripheral interface (SPI).

17. The system of claim 1, wherein:
the therapy screen of the smart communication device includes a user settings button configured to, in response to a user input, generate a signal to change the lightceutical clinical code.

* * * * *